United States Patent
Xiong et al.

(10) Patent No.: US 10,702,612 B2
(45) Date of Patent: Jul. 7, 2020

(54) CONJUGATED POLYMER-BASED NANOPROBE AND PREPARATION METHOD AND APPLICATION THEREOF

(71) Applicant: SHANGHAI JIAO TONG UNIVERSITY, Shanghai (CN)

(72) Inventors: Liqin Xiong, Shanghai (CN); Fengwen Cao, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 16/551,711

(22) Filed: Aug. 26, 2019

(65) Prior Publication Data

US 2019/0381195 A1 Dec. 19, 2019

Related U.S. Application Data

(63) Continuation of application No. PCT/CN2017/094222, filed on Jul. 25, 2017.

(30) Foreign Application Priority Data

Mar. 29, 2017 (CN) .......................... 2017 1 0199235

(51) Int. Cl.

| A61K 49/00 | (2006.01) |
|---|---|
| A61K 49/10 | (2006.01) |
| A61K 49/12 | (2006.01) |
| A61K 49/18 | (2006.01) |
| A61K 49/22 | (2006.01) |

(52) U.S. Cl.
CPC ...... *A61K 49/0002* (2013.01); *A61K 49/0032* (2013.01); *A61K 49/0034* (2013.01); *A61K 49/0084* (2013.01); *A61K 49/105* (2013.01); *A61K 49/126* (2013.01); *A61K 49/1812* (2013.01); *A61K 49/221* (2013.01); *A61K 49/227* (2013.01)

(58) Field of Classification Search
CPC combination set(s) only.
See application file for complete search history.

(56) References Cited

FOREIGN PATENT DOCUMENTS

| CN | 106474492 A | 3/2017 |
|---|---|---|
| WO | 2013154736 A1 | 10/2013 |

OTHER PUBLICATIONS

Hashim et al., Nanoscale, 2014,6, 8376 (Year: 2014).*
Xiong, Liqin et al. Self-luminescing BRET-FRET neat-infrared dots for in vivo lymph-node mapping and tumour imaging. Nature Communications. Nov. 13, 2012, vol. 3, pp. 1-9.
Gao fengwen et al. Folic acid functionalized PFBT fluorescent polymer dots for tumour imaging. Chin. J. Chem Feb. 3, 2016, 34(6), pp. 570-575.
Xiong, Liqin et al. Long-term-stable near-infrared polymer dots with ultrasmall size and narrow-band emission for imaging tumor vasculature in vivo. Bioconjungate Chemistry. Apr. 30, 2015, 26(5), pp. 817-821.

* cited by examiner

*Primary Examiner* — Robert S Cabral
(74) *Attorney, Agent, or Firm* — Wayne & Ken, LLC; Tony Hom

(57) ABSTRACT

Disclosed is a conjugated polymer-based nanoprobe, including a fluorescent conjugated polymer, a surface ligand, a target molecule, a near-infrared fluorescent dye and optionally a gadolinium-containing magnetic resonance contrast agent. This application also discloses a method for preparing the conjugated polymer-based nanoprobe, including: adding raw materials to an organic solvent followed by ultrasonication to obtain a mixture; and adding the mixture to ultrapure water and continuously ultrasonicating the reaction mixture. The conjugated polymer-based nanoprobe can be applied in a combined molecular imaging technique of near infrared fluorescence imaging, photoacoustic imaging and magnetic resonance imaging to effectively recognize metastatic lymph nodes and normal lymph nodes, and it can be retained in the metastatic lymph nodes for a long time, meeting the requirements for long-term observation. Moreover, the near-infrared fluorescent conjugated polymer-based nanoprobe can generate reactive oxygen under irradiation, which is suitable for the photodynamic treatment of tumors.

18 Claims, 25 Drawing Sheets

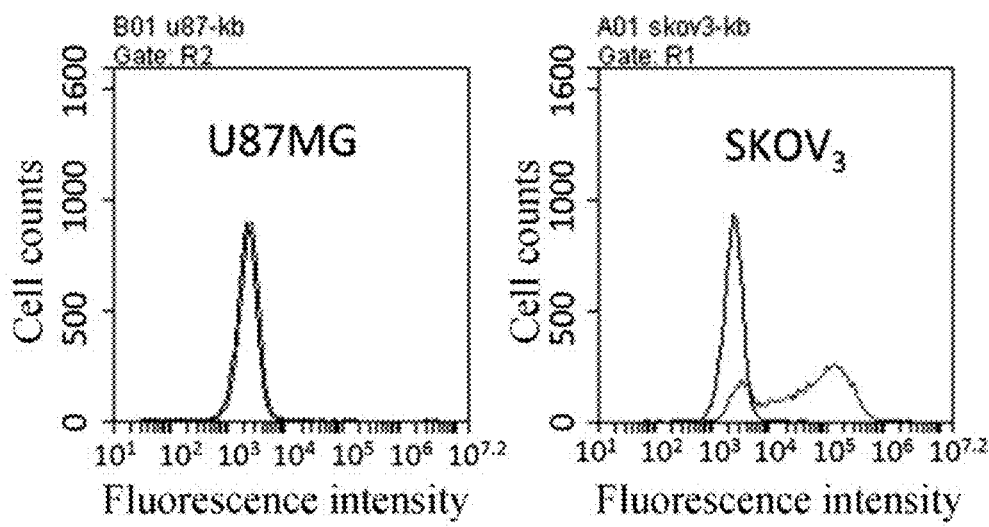
FIG. 11 A
FIG. 11B
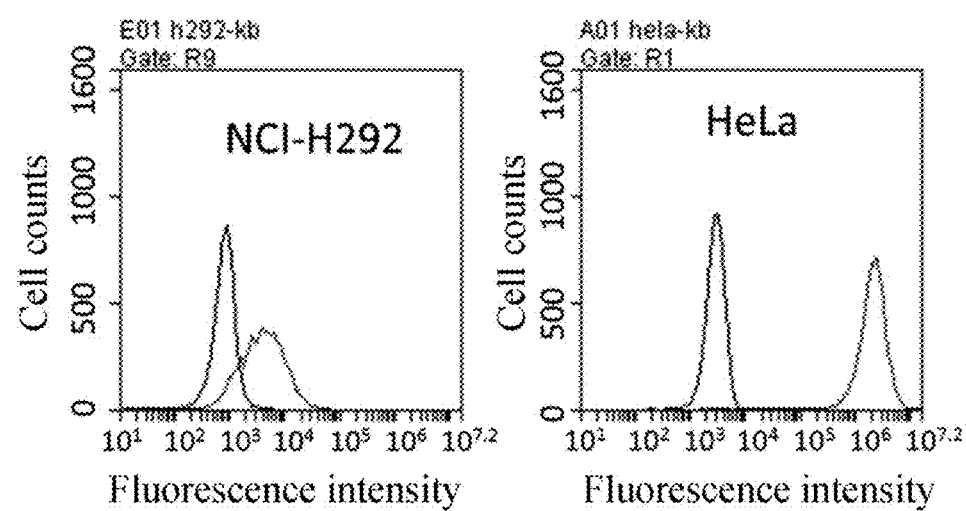
FIG. 11C
FIG. 11D

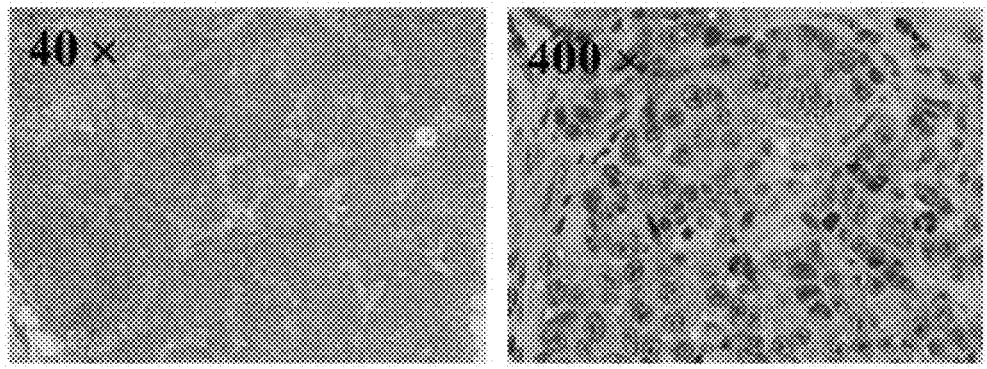
FIG. 26
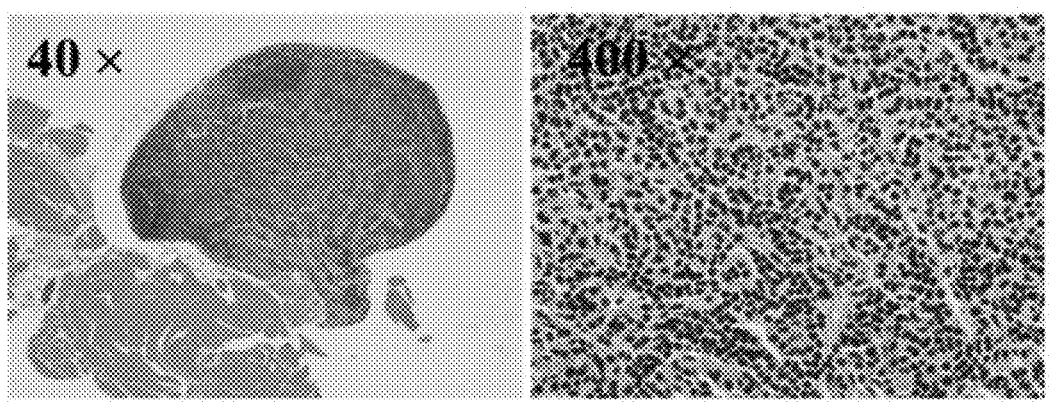
FIG. 27
FIG. 28

CONJUGATED POLYMER-BASED NANOPROBE AND PREPARATION METHOD AND APPLICATION THEREOF

CROSS-REFERENCE TO RELATED APPLICATIONS

This application is a continuation of International Patent Application No. PCT/CN2017/094222, filed on Jul. 25, 2017, which claims the benefit of priority from Chinese Patent Application No. 201710199235.1, filed on Mar. 29, 2017. The contents of the aforementioned application, including any intervening amendments thereto, are incorporated herein by reference in its entirety.

TECHNICAL FIELD

The present application relates to molecular imaging, and more specifically to a conjugated polymer-based nanoprobe, a preparation method and an application thereof, especially in the targeted imaging of lymph nodes with tumor metastasis by near-infrared fluorescence imaging, photoacoustic imaging and magnetic resonance imaging in a tumor model of lymph node metastasis.

BACKGROUND OF THE INVENTION

Most of the primary tumors, such as breast cancer, lung cancer, gastric cancer, esophageal cancer, thyroid cancer, cervical cancer, ovarian cancer, colorectal adenocarcinoma, pancreatic cancer and laryngeal cancer, generally metastasize by lymph nodes. Therefore, lymph node staging plays an important role not only in determining the therapeutic regimens and prognosis for most of the primary tumors, but also in accurately evaluating the extent of preoperative lymph node metastasis in clinic. However, the available probes (e.g., ICG) and imaging methods (e.g., PET/CT, magnetic resonance imaging and ultrasound) for detecting lymphatic metastasis in clinic fail to effectively recognize a normal lymph node from a lymph node with tumor metastasis. Moreover, the systematic lymphadenectomy will result in a large trauma and a higher occurrence of postoperative sequelae. It is more serious that some patients suffering from early cancer may passively undergo unnecessary lymphadenectomy treatment due to the failure in determining the status of lymph nodes. Given the above, if the status of the lymph node metastasis can be detected preoperatively and intraoperatively, the involving area of the tumor will be accurately determined, thereby greatly reducing the patient's pain and improving the life quality.

Molecular imaging is a tool by which the normal or pathological intracellular molecular process can be studied in vivo so as to the physiological and pathological changes in organisms at the molecular or cellular level, providing a new technique for in vivo monitoring of disease processes, in vivo tracing of gene therapy, evaluation of in vivo efficacy and research of law of in-vivo activity of functional molecules. This technique has the advantages of non-invasion, real-time and in-vivo monitoring, fine imaging, and high sensitivity and specificity. There are various imaging methods used in the molecular imaging to image the specific target in vivo and the core part is the design of molecular probes. Molecular imaging methods mainly include radionuclide imaging, magnetic resonance imaging, optical imaging, ultrasonic imaging and photoacoustic imaging, and each imaging modal has respective advantages and limitations. For example, the fluorescence imaging has advantages of high sensitivity, relatively low cost and simple operation, but its penetration depth is limited. The radionuclide imaging and the magnetic resonance imaging have no limitation on the penetration depth, but they respectively have the defects of low spatial resolution and low sensitivity. In addition, the information acquired by a single imaging modal is too limited to reflect the complexity and specificity of organisms. Therefore, the combination of multiple molecular imaging modals and the construction of a multi-modal molecular probe, which are complementary to each other, can provide more accurate and reliable imaging information for biomedical research.

Fluorescent conjugated polymer, as a fluorescent probe, has unique photophysical and photochemical properties. It has been first reported by Swager et al. from MIT in 1995 that the fluorescent conjugated polymer can amplify the fluorescence signal by hundreds of times due to a $\pi$-$\pi$* conjugated molecular wire structure, which contributes to the wide application of the fluorescent conjugated polymer in the detection of biomacromolecules such as nucleic acids and proteins, and biological micromolecules such as ATP and glucose. Moreover, due to the presence of $\pi$-$\pi$* conjugated molecular wire structure, the fluorescent conjugated polymer has some advantages over the conventional small-molecule fluorescent compounds, for example, (1) the fluorescent conjugated polymer has a better stability; (2) the electronic structure and the fluorescence emission wavelength of the conjugated polymer can be adjusted by changing and modifying the chemical structure; and (3) in the premise of not changing the binding constant, the response signal may be amplified by hundreds of times to improve the sensitivity of the detection. In addition, compared to the semiconductor quantum dots, the fluorescent conjugated polymer is free of any toxic metals, allowing for less toxicity. Thus, the fluorescent conjugated polymer has recently been considered as a desired tool to be applied in the molecular imaging. However, the light emitted by the reported fluorescent conjugated polymer nanomaterials is mainly visible light, so that these materials are not very suitable for the in vivo imaging of small animals. Furthermore, fluorescent conjugated polymer nanoprobe-based targeted imaging has also not been reported to be used in the detection of lymph node metastasis.

Therefore, there is an urgent need for those skilled in the art to develop a conjugated polymer nanoprobe and a preparation method thereof for multi-modal molecular imaging, benefiting the targeted imaging of the lymph node metastasis and the differentiation between a normal lymph node and a lymph node with tumor metastasis.

SUMMARY OF THE INVENTION

An object of this application is to provide a conjugated polymer-based nanoprobe and a preparation method and an application thereof to overcome the defects of the single-modal imaging in the prior art and improve the probe used in the targeted imaging of lymph node metastasis.

In order to achieve the above object, a first aspect of the invention provides a conjugated polymer-based nanoprobe, comprising:

a fluorescent conjugated polymer;
a surface ligand;
a target molecule; and
a near-infrared fluorescent dye;

wherein, the surface ligand is provided on a surface of the conjugated polymer-based nanoprobe; the target molecule is provided on the surface of the conjugated polymer-based nanoprobe; the near-infrared fluorescent dye is provided in the conjugated polymer-based nanoprobe; the surface ligand plays a role in improving the biocompatibility of the probe and providing a carboxyl group for further coupling with an antibody or a protein; and the target molecule is capable of binding to a receptor on a tumor cell to form a binding between the probe and the tumor cell.

In an embodiment, the target molecule is capable of recognizing a folate receptor.

In an embodiment, the target molecule is a phospholipid-modified target molecule.

In an embodiment, the phospholipid modification is performed using a liposome.

In an embodiment, the phospholipid-modified target molecule is one or more of a phosphatidylethanolamine-polyethylene glycol 5000-folic acid conjugate, a phosphatidylethanolamine-polyethylene glycol 2000-folic acid conjugate and a phosphatidylethanolamine-folic acid conjugate.

In an embodiment, the surface ligand is a surface ligand modified with a terminal carboxyl. In an embodiment, the surface ligand is selected from styrene-polyethylene glycol-carboxyl (PS-PEG-COOH), polyethylene glycol-carboxyl (PEG-COOH), a styrene-maleic anhydride copolymer (PSMA) or a combination thereof.

In an embodiment, an absorption wavelength of the near-infrared fluorescent dye is 700-900 nm. In an embodiment, the near-infrared fluorescent dye is selected from the group consisting of NIR775, DiIC18, ICG, Cy7 and Cy7.5.

In an embodiment, the fluorescent conjugated polymer is selected from PFBT or MEH-PPV.

In an embodiment, a molecular weight of PFBT is 10,000-52,000 and a molecular weight of MEH-PPV is 10,142-200,000.

In an embodiment, a molecular weight of PFBT is 10,000-20,000, 39,000, 47,000 or 52,000 and a molecular weight of MEH-PPV is 10,142 or 200,000.

In an embodiment, the near-infrared fluorescent dye is 0.2%-1.2% by weight of the fluorescent conjugated polymer; a weight ratio of the surface ligand to the fluorescent polymer is 0.5-2:1; and a weight ratio of the target molecule to the fluorescent conjugated polymer is 0.2-1:1.

In an embodiment, using a transmission electron microscope, the conjugated polymer-based nanoprobe has an average particle size of 2-100 nm, preferably 20-60 nm.

In an embodiment, the conjugated polymer-based nanoprobe further comprises a gadolinium-containing magnetic resonance contrast agent, wherein the gadolinium-containing magnetic resonance contrast agent is provided at the surface of the conjugated polymer-based nanoprobe.

In an embodiment, the gadolinium of the gadolinium-containing magnetic resonance contrast agent is phospholipid-modified gadolinium.

In an embodiment, the phospholipid-modified gadolinium is a phospholipid-modified gadolinium-diethylenetriaminepentaacetic acid (DTPA) complex, which is selected from DTPA-BSA (Gd), bis(18:0 PE)-DTPA (Gd), bis(16:0 PE)-DTPA (Gd), bis(14:0 PE)-DTPA (Gd), 18:0 PE-DTPA (Gd), 16:0 PE-DTPA (Gd) or a combination thereof.

In an embodiment, the near-infrared fluorescent dye is 0.2%-1.2% by weight of the fluorescent conjugated polymer; a weight ratio of the surface ligand to the fluorescent conjugated polymer is 0.5-2:1; a weight ratio of the target molecule to the fluorescent conjugated polymer is 0.2-1:1; and a weight ratio of the gadolinium-containing magnetic resonance contrast agent to the fluorescent conjugated polymer is 3-5:1.

In an embodiment, using the transmission electron microscope, the conjugated polymer-based nanoprobe has an average particle size of 20-130 nm, preferably 30-60 nm.

A second aspect of the invention provides a method for preparing a conjugated polymer-based nanoprobe. In an embodiment, the conjugated polymer-based nanoprobe is the conjugated polymer-based nanoprobe without a gadolinium-containing magnetic resonance contrast agent, and the method correspondingly comprises the following steps:

(1) adding a fluorescent conjugated polymer, a surface ligand, a near-infrared fluorescent dye and a target molecule to an organic solvent followed by ultrasonication to obtain a mixture; and (2) adding the mixture to ultrapure water under ultrasonication and continuously ultrasonicating the reaction mixture.

In another embodiment, the conjugated polymer-based nanoprobe is the conjugated polymer-based nanoprobe with the gadolinium-containing magnetic resonance contrast agent, of which a preparation method further comprises: adding the gadolinium-containing magnetic resonance contrast agent to the organic solvent in step (1).

In an embodiment, the target molecule is a phospholipid-modified target molecule.

In an embodiment, the gadolinium of the gadolinium-containing magnetic resonance contrast agent is phospholipid-modified gadolinium.

In an embodiment, in step (2), a power for ultrasonication is set to 8-12%, the ultrasonication is performed for 4-6 s every other 2-4 s, and a total ultrasonication time is set to 50-70 s. In an embodiment, the power for ultrasonication is set to 10%, the ultrasonication is performed for 5 s every other 3 s, and the total ultrasonication time is set to 60 s. In an embodiment, a weight ratio of the gadolinium-containing magnetic resonance contrast agent to the fluorescent conjugated polymer is 3-5:1.

In an embodiment, in step (1), the organic solvent is tetrahydrofuran or chloroform.

In an embodiment, the near-infrared fluorescent dye is 0.2%-1.2% by weight of the fluorescent conjugated polymer; a weight ratio of the surface ligand to the fluorescent conjugated polymer is 0.5-2:1; and a weight ratio of the target molecule to the fluorescent conjugated polymer is 0.2-1:1.

In an embodiment, the method further comprises: step (3) introducing nitrogen to the reaction mixture under heating to volatilize the organic solvent to prepare the conjugated polymer-based nanoprobe.

In an embodiment, in step (3), a temperature of the heating is 45-55° C., preferably 50° C.

A third aspect of the invention provides an application of a conjugated polymer-based nanoprobe in the preparation of a molecular imaging agent. In an embodiment, the conjugated polymer-based nanoprobe is the conjugated polymer-based nanoprobe without a gadolinium-containing magnetic resonance contrast agent, which can be used for near-infrared fluorescence imaging and/or photoacoustic imaging.

In another embodiment, the conjugated polymer-based nanoprobe is the conjugated polymer-based nanoprobe with the gadolinium-containing magnetic resonance contrast agent, which can be used for near-infrared fluorescence imaging, photoacoustic imaging and/or magnetic resonance imaging.

In an embodiment, the conjugated polymer-based nanoprobe is capable of targetedly imaging tumor cells expressing a folate receptor at the cellular level.

In an embodiment, the conjugated polymer-based nanoprobe is capable of recognizing a normal lymph node and a lymph node with tumor metastasis.

In an embodiment, the conjugated polymer-based nanoprobe is capable of recognizing the normal lymph node and the lymph node with tumor metastasis at the in vivo small animal level.

A fourth aspect of the invention provides a molecular imaging agent. In an embodiment, the molecular imaging agent comprises any one of the conjugated polymer-based nanoprobes as described above.

A fifth aspect of the invention provides an application of a conjugated polymer-based nanoprobe in the preparation of a photodynamic therapy agent. In an embodiment, the conjugated polymer-based nanoprobe is any one of the conjugated polymer-based nanoprobes described above.

In an embodiment, the conjugated polymer-based nanoprobe comprises a near-infrared fluorescent dye, wherein the near-infrared fluorescent dye is capable of generating reactive oxygen under irradiation.

In an embodiment, the near-infrared fluorescent dye is a near-infrared dye containing a tetrapyrrolyl structure.

In an embodiment, the near-infrared fluorescent dye is NIR775.

A sixth aspect of the invention provides a photodynamic therapy agent. In an embodiment, the photodynamic therapy agent comprises any one of the conjugated polymer-based nanoprobes as described above.

In an embodiment, the conjugated polymer nanoprobe comprises a near-infrared fluorescent dye, wherein the near-infrared fluorescent dye is capable of generating reactive oxygen under irradiation.

In an embodiment, the near-infrared fluorescent dye is a near-infrared dye containing a tetrapyrrolyl structure.

In an embodiment, the near-infrared fluorescent dye is NIR775.

In an embodiment, the photodynamic therapy agent can be used in the photodynamic therapy of a tumor.

In an embodiment, the photodynamic therapy agent is capable of killing the tumor cells at the cellular level and the in vivo small animal level.

In an embodiment, the tumor is a subcutaneous solid tumor.

This application has the following beneficial effects.

The hybrid fluorescent conjugated polymer-based nanoprobe of the invention can be used for multi-modal imaging and can also target a folate receptor, capable of targetedly imaging tumor cells expressing the folate receptor at the cellular level. Moreover, in a tumor model of lymphatic metastasis, the nanoprobe can effectively identify a metastatic lymph node and a normal lymph node, and it can be retained in the metastatic lymph node for a long time, suitable for the long-term observation and detection. The hybrid fluorescent conjugated polymer-based nanoprobe prepared by the invention can effectively identify the lymph node with tumor metastasis in a tumor model of the lymphatic metastasis, and its specific targeted imaging effect on the lymphatic metastasis can reach or exceed the level of the prior art.

Furthermore, the conjugated polymer-based nanoprobe is directly prepared by a coprecipitation method, where the process is simple and highly-efficient. Since the target molecule and the gadolinium-containing magnetic resonance contrast agent both are modified with a phospholipid, they can cross-link with the fluorescent conjugated polymer-based nanoprobe closely and stably after the ultrasonication, avoiding the leakage of a small molecule from the nanoprobe. Therefore, the conjugated polymer-based nanoprobe can be prepared by one step. Furthermore, after the ultrasonication, the entire nanoprobe is coated tighter with the surface ligand, which further prevents the leakage of the small molecule, improving the stability of the entire nanoprobe and facilitating the storage of the nanoprobe.

The hybrid fluorescent conjugated polymer-based nanoprobe of the invention is suitable for the combined molecular imaging technique of near-infrared fluorescence imaging, photoacoustic imaging and magnetic resonance imaging to targetedly image the metastatic lymph node at small animal level in vivo, which is applicable to the imaging-mediated surgical navigation to perform the dissection of metastatic lymph nodes at an increased dissection rate. The conjugated polymer-based nanoprobe mixed with a near-infrared fluorescent dye of the invention can generate reactive oxygen under irradiation, suitable for the photodynamic therapy of tumors, especially the subcutaneous solid tumors. Moreover, this conjugated polymer-based nanoprobe also has good effect and low cytotoxicity, allowing for a good application prospect in photodynamic therapy.

BRIEF DESCRIPTION OF THE DRAWINGS

The invention will be described below in detail with reference to the accompanying drawings to make the objects, features and effects of the invention fully understood.

FIGS. 11A-D are flow cytometry showing the expression of respective folate receptors of human U87MG glioma cell line, human SKOV$_3$ ovarian carcinoma cell line, human NCI-H292 lung cancer cell line with lymph node metastasis and human HeLa cervical carcinoma cell line.

FIG. 26 shows the H & E staining of tissues of the mouse with NCI-H292 tumor in the in vivo photodynamic therapy using the hybrid fluorescent conjugated polymer-based nanoprobe.

FIG. 27 shows the H & E staining of NCI-H292 tumor tissue.

FIG. 28 shows the H & E staining of normal lymph nodes.

DETAILED DESCRIPTION OF EMBODIMENTS

Unless otherwise defined, the techniques and terms used herein have the same meaning as commonly understood by those skilled in the art.

Unless otherwise specified in the description and claims, terms "comprising", "including", etc., should be considered to be inclusive rather than exclusive or exhaustive, that is, they have the meaning of "including but not limited to".

Abbreviations of the compounds used herein are shown as follows:

DSPE-PEG (5000) Folate: phosphatidylethanolamine-polyethylene glycol 5000-folic acid conjugate;

DSPE-PEG (2000) Folate: phosphatidylethanolamine-polyethylene glycol 2000-folic acid conjugate;

PE-Folate: phosphatidylethanolamine-folic acid conjugate;

PS-PEG-COOH: styrene-polyethylene glycol-carboxyl;

PEG-COOH: polyethylene glycol-carboxyl;

PSMA: styrene-maleic anhydride copolymer;

PFBT: poly (9,9-dioctylfluorene-alt-benzothiadiazole);

MEH-PPV: poly [2-methoxy-5-(2'-ethylhexyloxy)-1,4-phenylenevinylene];

ADMA: 9,10-anthracenediyl-bis (methylene) dimalonic acid;

DCFH-DA: 2',7'-dichlorodihydrofluorescein diacetate;

DCF: dichlorofluorescein;

PI: propidium iodide;

AX: axillary lymph nodes;

PO: popliteal lymph nodes;
SC: hip lymph nodes;
IN: inguinal lymph nodes; and
THF: tetrahydrofuran.

Unless otherwise specified, materials used herein such as near-infrared fluorescent dyes NIR775, DiIC18, ICG, Cy7 and Cy7.5, are commercially available. A first aspect of the invention provides a fluorescent conjugated polymer-based nanoprobe, which has a structure as shown in FIG. 1 or 2.

Figure 1:
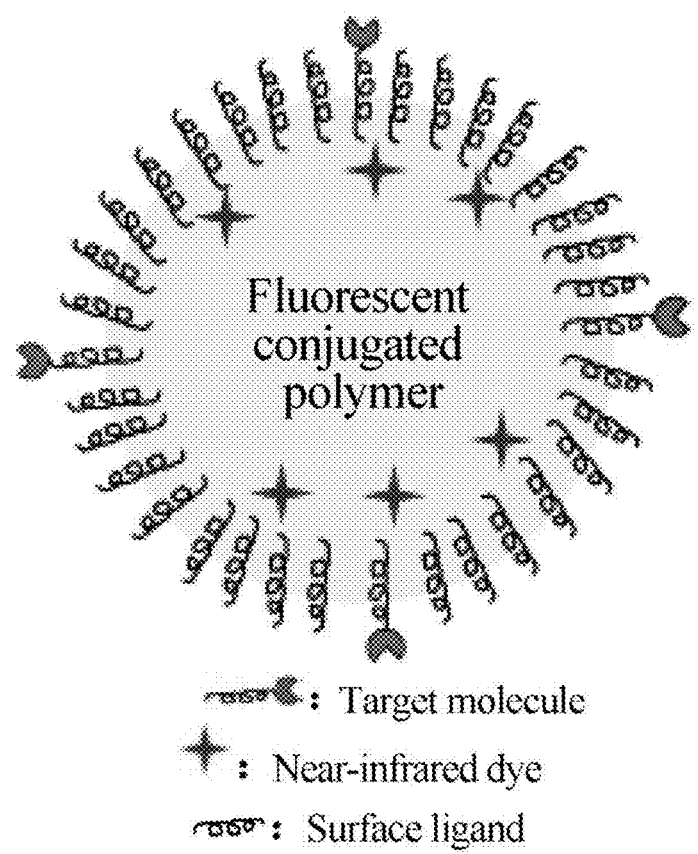
FIG. 1 schematically shows a structure of a fluorescent conjugated polymer-based nanoprobe according to an embodiment of the invention.

The fluorescent conjugated polymer-based nanoprobe as shown in FIG. 1 includes a fluorescent conjugated polymer, a surface ligand, a target molecule and a near-infrared fluorescent dye.

Figure 2:
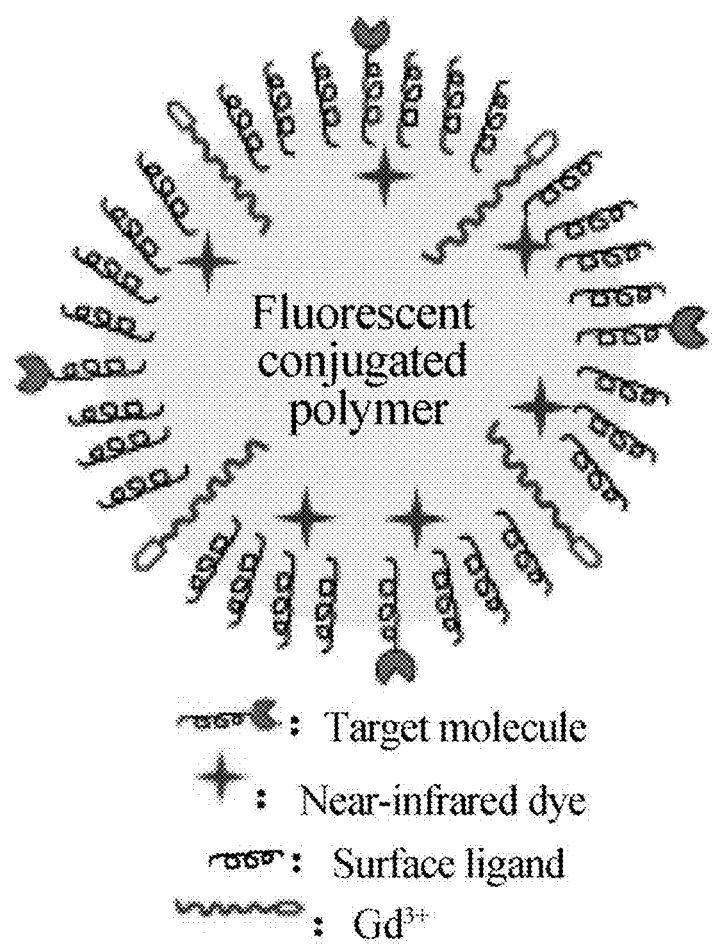
FIG. 2 schematically shows a structure of a fluorescent conjugated polymer-based nanoprobe according to another embodiment of the invention.

The fluorescent conjugated polymer-based nanoprobe as shown in FIG. 2 includes a fluorescent conjugated polymer, a surface ligand, a target molecule, a near-infrared fluorescent dye and a gadolinium-containing magnetic resonance contrast agent.

The fluorescent conjugated polymer is PFBT or MEH-PPV varying in molecular weight.

The target molecule includes DSPE-PEG (5000) Folate, DSPE-PEG (2000) Folate, PE-Folate and a combination thereof.

The surface ligand includes PS-PEG-COOH, PEG-COOH, PSMA and a combination thereof.

$Gd^{3+}$ (the gadolinium-containing magnetic resonance contrast agent) includes DTPA-BSA (Gd), bis(18:0 PE)-DTPA (Gd), bis (16:0 PE)-DTPA (Gd), bis(14:0 PE)-DTPA (Gd), 18:0 PE-DTPA (Gd), 16:0 PE-DTPA (Gd) and a combination thereof.

Such compounds are specifically described as follows.

The monomer of PFBT is shown as follows:

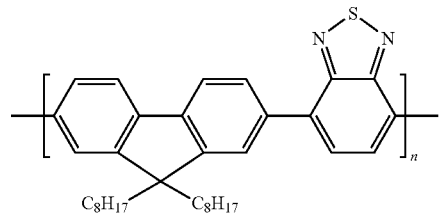

where the PFBT has a molecular weight of 10,000-52,000.

The monomer of MEH-PPV is shown as follows:

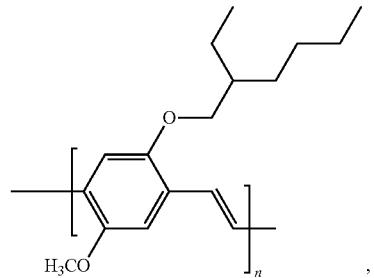

where the MEH-PPV has a molecular weight of 10,000-200,000.

DSPE-PEG (5000) is shown as follows:

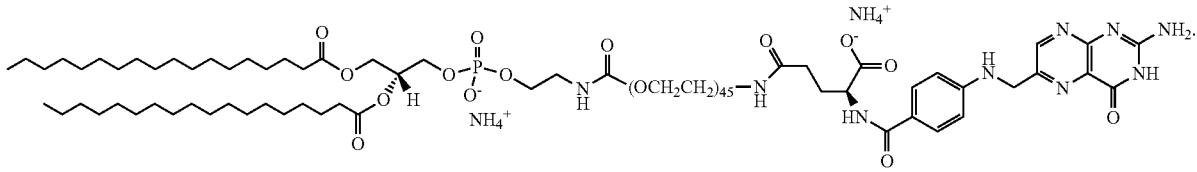

DSPE-PEG (2000) is shown as follows:

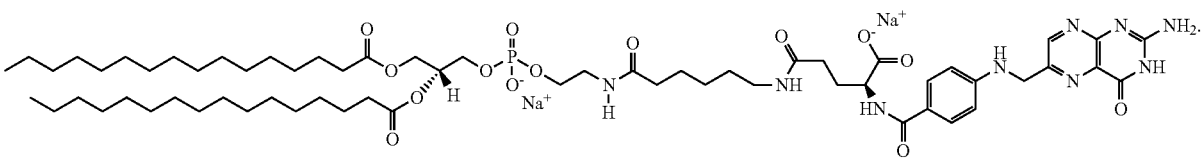 [SMILES: [Na+] ; CCCCCCCCCCCCCCCC(=O)OC[C@H](COP(=O)([O-])OCCNC(=O)CCCCCNC(=O)CC[C@H](NC(=O)c1ccc(NCc2cnc3nc(N)[nH]c(=O)c3n2)cc1)C(=O)[O-])OC(=O)CCCCCCCCCCCCCCC ; [Na+]]

PE-Folate is shown as follows:

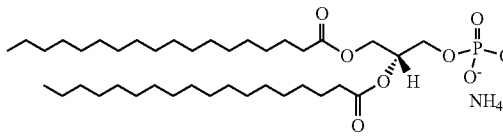
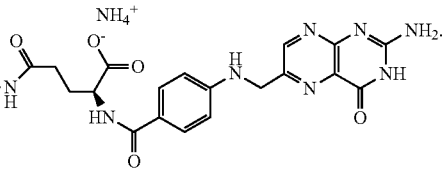

NIR775 is shown as follows:
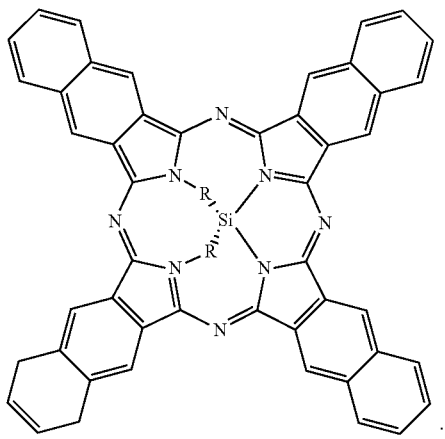
R = O—Si((CH$_2$)$_5$CH$_3$)$_3$
DiIC18 is shown as follows:
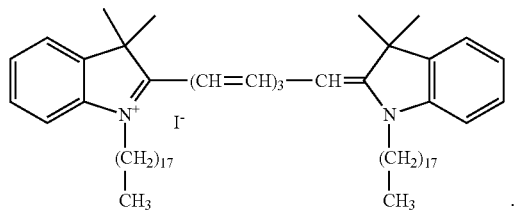
Cy7 is shown as follows:
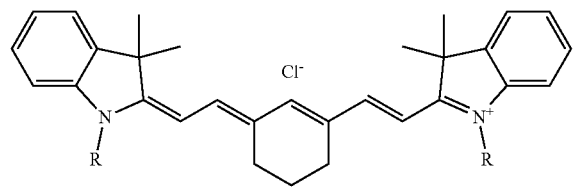
where R=
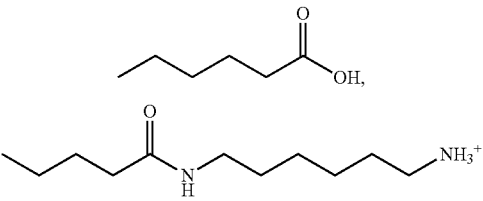
or other hydrophobic chains.
Cy7.5 is shown as follows:
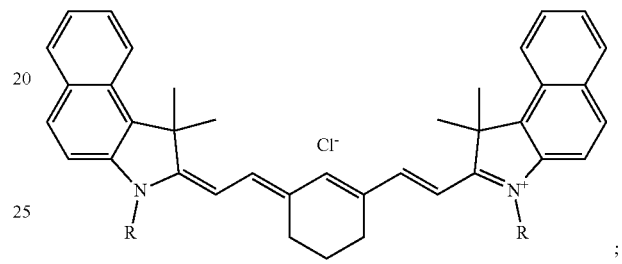
where R=
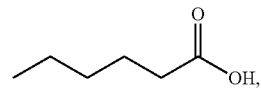
or other hydrophobic chains.
DTPA-BSA (Gd) is shown as follows:
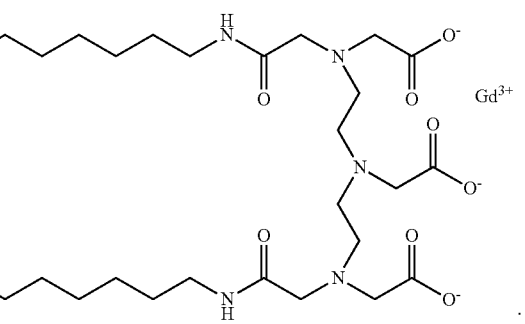

Bis(18:0 PE)-DTPA (Gd) is shown as follows:
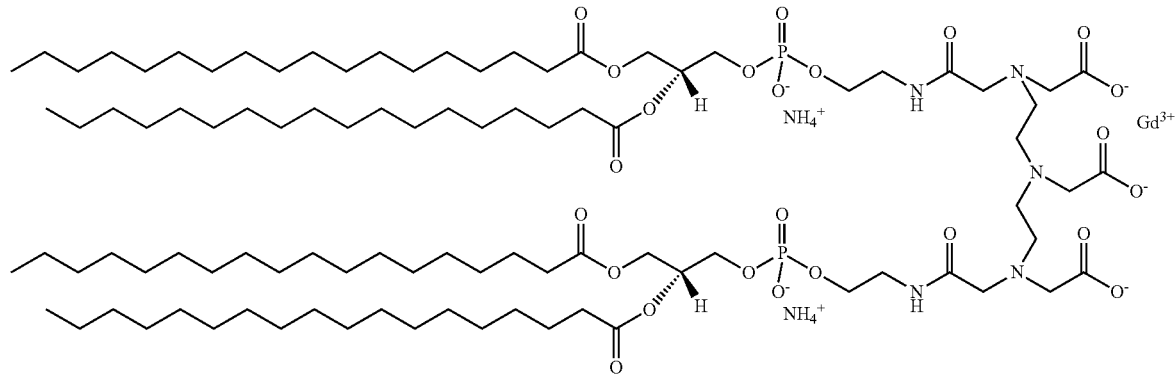
Bis(16:0 PE)-DTPA (Gd) is shown as follows:
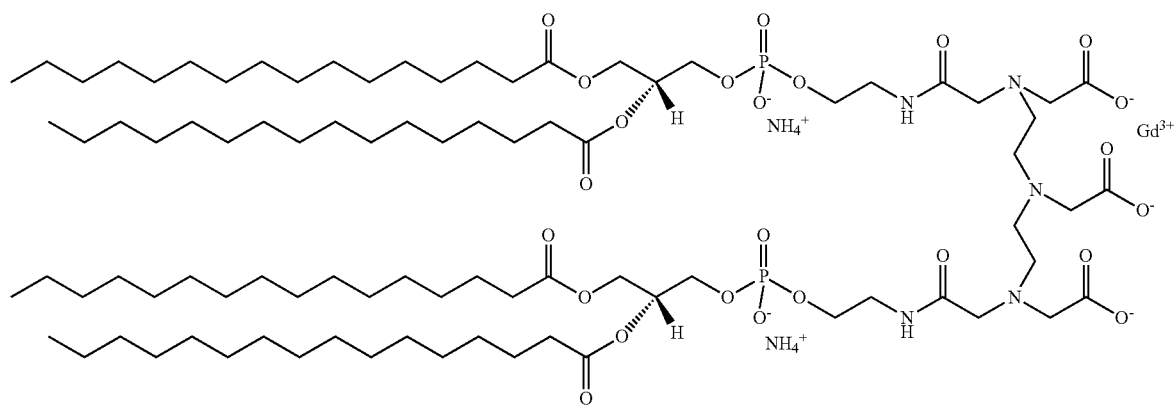
Bis(14:0 PE)-DTPA (Gd) is shown as follows:
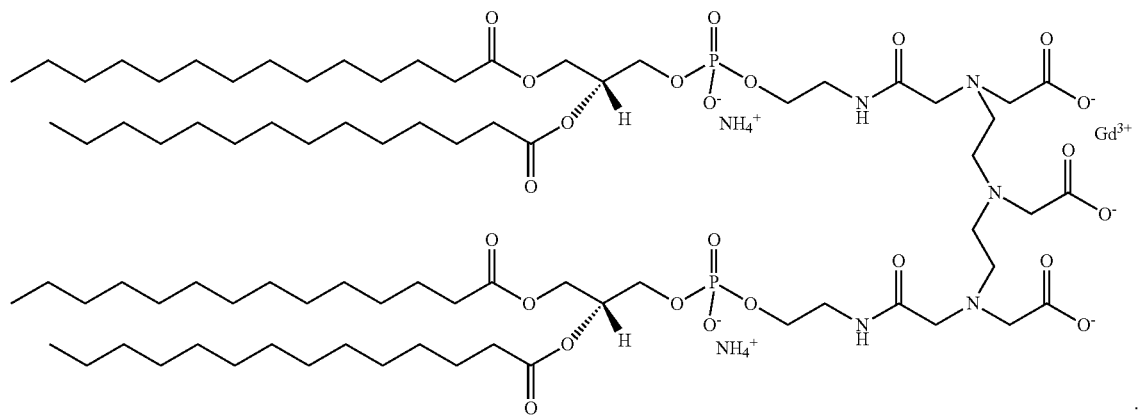

18:0 PE-DTPA (Gd) is shown as follows:

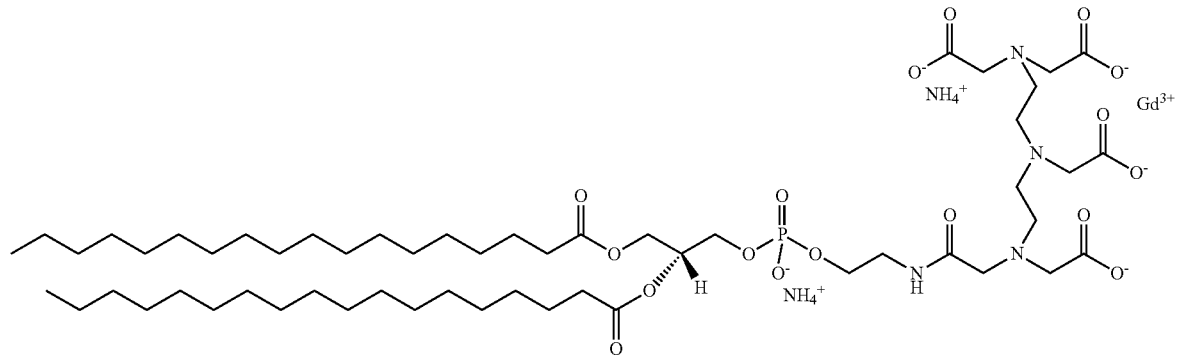

16:0 PE-DTPA (Gd) is shown as follows:

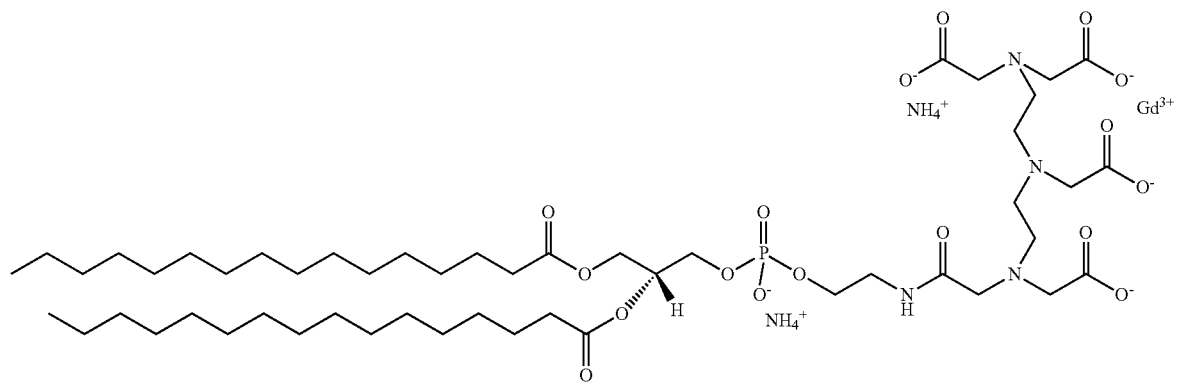

PS-PEG-COOH is shown as follows:

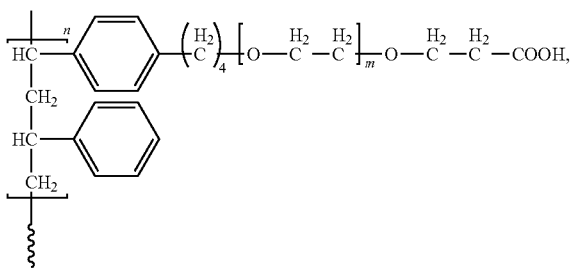

where the PS has a molecular weight of 6,500-21,700 Da and the PEG has a molecular weight of 1,200-4,600 Da.

PEG-COOH is shown as follows:

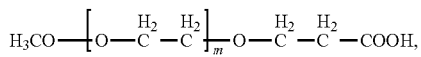

where the PEG has a molecular weight of 2,000-5,000.

A second aspect of the invention provides a method for preparing a conjugated polymer-based nanoprobe, which involves a coprecipitation process, specifically, a mixed solution of a fluorescent conjugated polymer, a near-infrared fluorescent dye, a target molecule and a surface ligand in an organic solvent (i.e., THF) or a mixed solution of a fluorescent conjugated polymer, a near-infrared fluorescent dye, a target molecule, a surface ligand and a gadolinium-containing magnetic resonance contrast agent in an organic solvent (i.e., THF) was rapidly added to water and ultrasonicated to form the conjugated polymer-based nanoprobe.

A third aspect of the invention provides an application of the conjugated polymer-based nanoprobe, specifically, the conjugated polymer nanoprobe, as shown in FIG. 1, can be used for the near-infrared fluorescence imaging and/or the photoacoustic imaging; and the conjugated polymer nanoprobe as shown in FIG. 2 can be used for the near-infrared fluorescence imaging, the photoacoustic imaging and/or the magnetic resonance imaging.

The two types of conjugated polymer-based nanoprobes as described above are capable of targetedly imaging tumor cells expressing the folate receptor at the cellular level. Moreover, they are also capable of identifying a normal lymph node and a metastatic lymph node, especially capable of identifying the normal lymph node and the lymph node with tumor metastasis at in vivo small animal level.

A fourth aspect of the invention provides a molecular imaging agent comprising the conjugated polymer-based nanoprobe as described above.

A fifth aspect of the invention provides an application of the above conjugated polymer-based nanoprobe in the preparation of a photodynamic therapy agent. The photodynamic therapy is specifically described as follows: a photosensitizer is introduced into a human body; after a certain period, the lesion site is irradiated with light of a specific wavelength to generate singlet oxygen and/or free radicals in the presence of molecular oxygen through a series of photochemical and photobiological reactions. Then the singlet oxygen and/or free radicals can oxidatively destroy various biological macromolecules in cells and tissues, which causes irreversible damage to the cells with active abnormal hyperplasia, eventually killing the cells for therapeutic purposes.

A six aspect of the invention provides a photodynamic therapy agent comprising any one of the above conjugated polymer-based nanoprobes. In an embodiment, the photodynamic therapy agent comprises a near-infrared fluorescent dye, which is capable of generating reactive oxygen under irradiation. In addition, the conjugated polymer-based nanoprobe has lower or no toxicity.

The invention will be described in detail with reference to the embodiments.

Example 1

Preparation of a Hybrid NIR775-PFBT Fluorescent Conjugated Polymer-Based Nanoprobe 1,450 µL of a filtered tetrahydrofuran solution was added to an EP tube. The EP tube was then sequentially added with 250 µL of a PFBT solution (1 mg/mL), 250 µL of a PS-PEG-COOH solution (1 mg/mL), 3 µL of a NIR775 solution (1 mg/mL) and 50 µL of a phospholipid-folic acid solution (1 mg/mL) and ultrasonicated for 3 min to obtain a mixture. The mixture was quickly added to 10 mL of ultrapure water under ultrasonication, where a power for the ultrasonication was set at 10%, the ultrasonication is performed for 5 s every other 3 s, and a total ultrasonication time was 1 min. After the ultrasonication was completed, nitrogen was introduced at 50° C. for 25 min to completely volatilize the THF in the solution, and thus the hybrid NIR775-PFBT fluorescent conjugated polymer-based nanoprobe was obtained.

Figure 3:
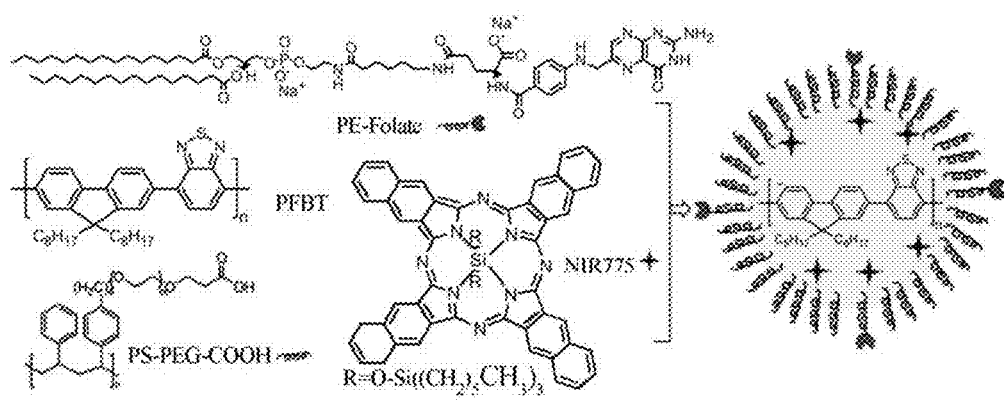
FIG. 3 schematically shows the preparation of the probe in Example 1.
Figure 4:
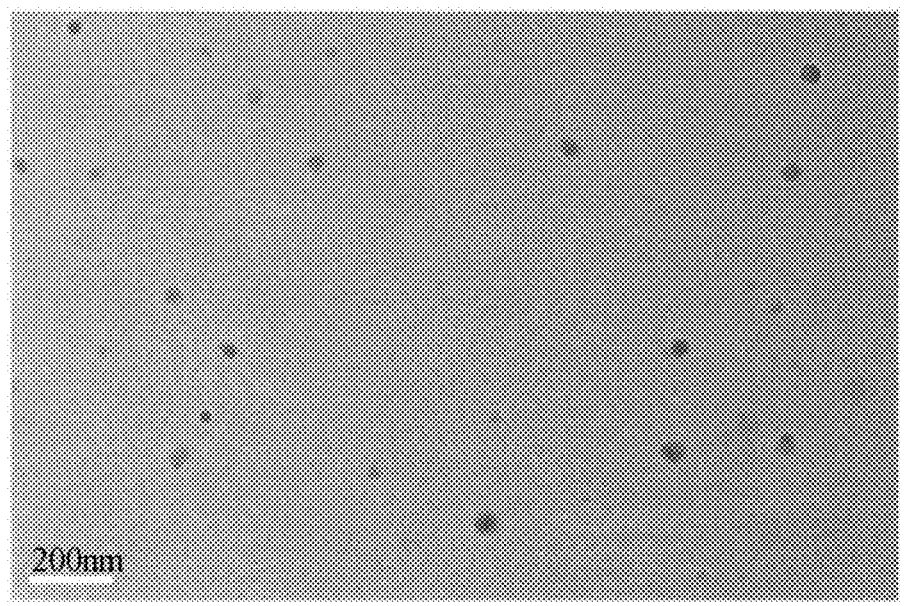
FIG. 4 is an electron micrograph of the probe in Example 1.

The above preparation process was schematically shown in FIG. 3. As shown in FIG. 4, the prepared hybrid NIR775-fluorescent conjugated polymer-based nanoprobe had an average particle size of about 30 nm under a transmission electron microscope.

Example 2

Preparation of a Hybrid NIR775-Gd$^{3+}$-PFBT Fluorescent Conjugated Polymer-Based Nanoprobe 650 µL of a filtered tetrahydrofuran solution was added into the EP tube. The EP tube was then sequentially added with 250 µL of a PFBT solution (1 mg/mL), 250 µL of a surface ligand PS-PEG-COOH solution (1 mg/mL), 3 µL of a NIR775 solution (1 mg/mL), 50 µL of a phospholipid-folic acid solution (1 mg/mL) and 800 µL of a gadolinium-containing magnetic resonance contrast agent DTPA-BSA (Gd) solution (1.25 mg/mL) and ultrasonicated for 3 min to obtain a mixture. The mixture was quickly added to 10 mL of ultrapure water under ultrasonication, where a power for the ultrasonication was set at 10%, the ultrasonication is performed for 5 s every other 3 s, and a total ultrasonication time was 1 min. After the ultrasonication was completed, nitrogen was introduced at 50° C. for 25 min to completely volatilize the THF in the solution, and thus the hybrid NIR775-Gd$^{3+}$-PFBT fluorescent conjugated polymer-based nanoprobe was obtained.

Figure 5:
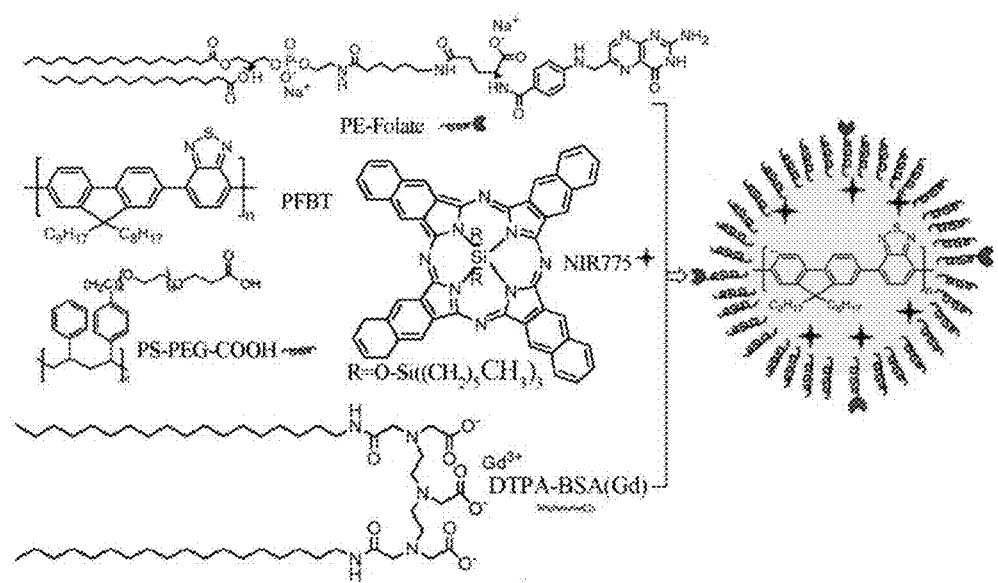
FIG. 5 schematically shows the preparation of the probe in Example 2.
Figure 6:
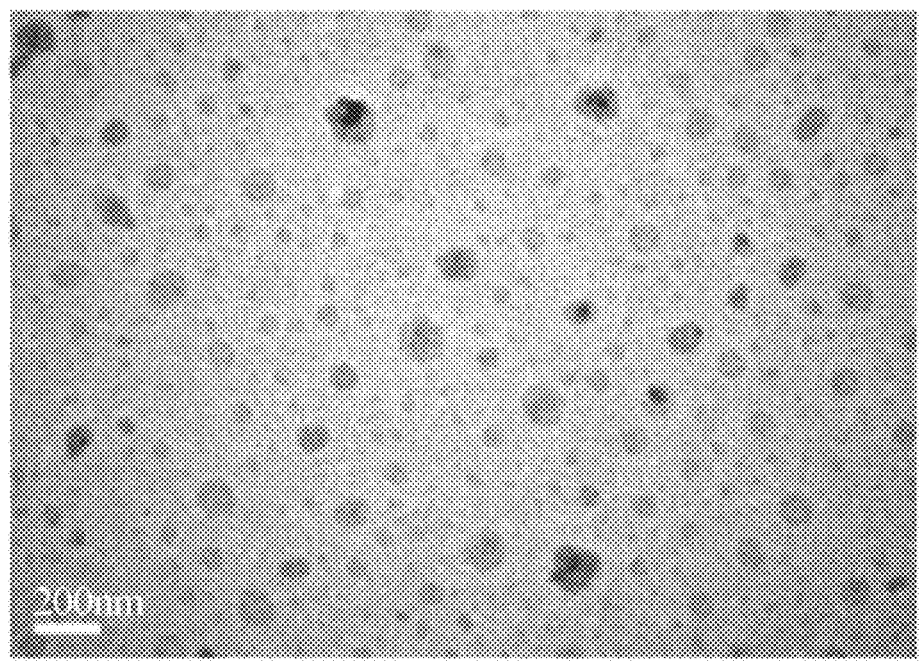
FIG. 6 is an electron micrograph of the probe in Example 2.

The above preparation process was schematically shown in FIG. 5. As shown in FIG. 6, the hybrid NIR775-Gd$^{3+}$-fluorescent conjugated polymer nanoprobe had an average particle size of about 50 nm under a transmission electron microscope.

Example 3

Preparation of a Hybrid NIR775-MEH-PPV Fluorescent Conjugated Polymer-Based Nanoprobe 1,450 µL of a filtered tetrahydrofuran solution was added to an EP tube. The EP tube was then sequentially added with 250 µL of a MEH-PPV solution (1 mg/mL), 250 µL of a surface ligand PS-PEG-COOH solution (1 mg/mL), 3 µL of a NIR775 solution (1 mg/mL) and 50 µL of a phospholipid-folic acid solution (1 mg/mL) and ultrasonicated for 3 min to obtain a mixture. The mixture was quickly added to 10 mL of ultrapure water under ultrasonication, where a power for the ultrasonication was set at 10%, the ultrasonication is performed for 5 s every other 3 s, and a total ultrasonication time was 1 min. After the ultrasonication was completed, nitrogen was introduced at 50° C. for about 25 min to completely volatilize the THF in the solution, and thus the hybrid NIR775-fluorescent conjugated polymer-based nanoprobe was obtained. The hybrid NIR775-fluorescent conjugated polymer-based nanoprobe was shown under a transmission electron microscope to have an average particle size of about 20-30 nm.

Example 4

Preparation of a Hybrid NIR775-Gd3$^+$-MEH-PPV Fluorescent Conjugated Polymer-Based Nanoprobe 650 µL of a filtered tetrahydrofuran solution was added to an EP tube. The EP tube was then sequentially added with 250 µL of a MEH-PPV solution (1 mg/mL), 250 µL of a surface ligand PS-PEG-COOH solution (1 mg/mL), 3 µL of a NIR775 solution (1 mg/mL), 50 µL of a phospholipid-folic acid solution (1 mg/mL) and 800 µL of a gadolinium-containing magnetic resonance contrast agent DTPA-BSA (Gd) solution (1.25 mg/mL) and ultrasonicated for 3 min to obtain a mixture. The mixture was quickly added to 10 mL of ultrapure water under ultrasonication, where a power for the ultrasonication was set at 10%, the ultrasonication is performed for 5 s every other 3 s, and a total ultrasonication time was 1 min. After the ultrasonication was completed, nitrogen was introduced at 50° C. for about 25 min to completely volatilize the THF in the solution, and thus the hybrid NIR775-Gd3$^+$-MEH-PPV fluorescent conjugated polymer-based nanoprobe was obtained. The hybrid NIR775-Gd3$^+$-fluorescent conjugated polymer-based nanoprobe was shown under a transmission electron microscope to have an average particle size oft about 40-50 nm.

Example 5

Fluorescence Spectrum Analysis of the Nanoprobe 1 mL of the probe solution was added to a quartz dish for the test of fluorescence excitation and fluorescence emission spectrums, where the test was performed on an Edinburgh fluorescence spectrometer LFS-920, and the related experimental parameters were set as follows: scanning parameters of the fluorescence excitation spectrum: receiving wavelength: 776 nm, and excitation waveband: 350-750 nm; scanning parameters of the fluorescence emission spectrum: excitation wavelength: 465 nm, and receiving waveband: 500-850 nm; scanning interval: 2 nm; slit width:5 nm; and voltage: 400 V.

Figure 7:
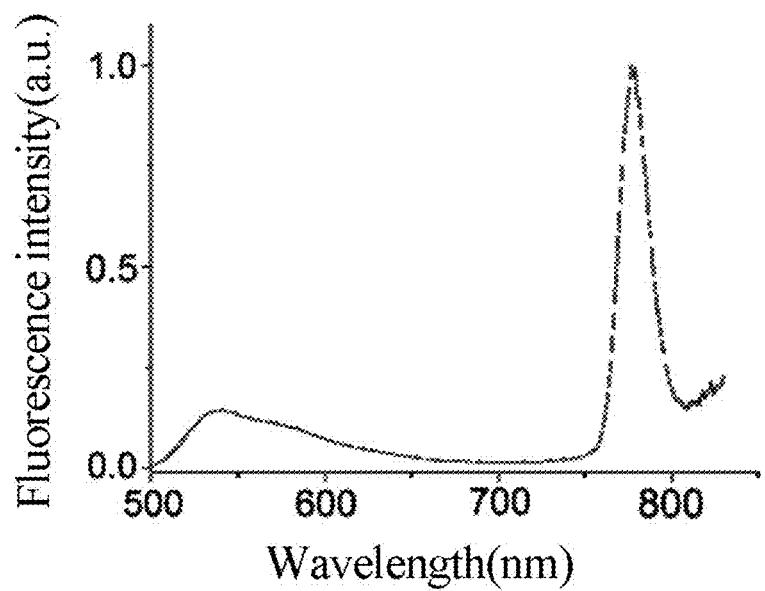
FIG. 7 is a near-infrared fluorescence spectrum of a hybrid NIR775-PFBT fluorescent conjugated polymer-based nanoprobe.
Figure 8:
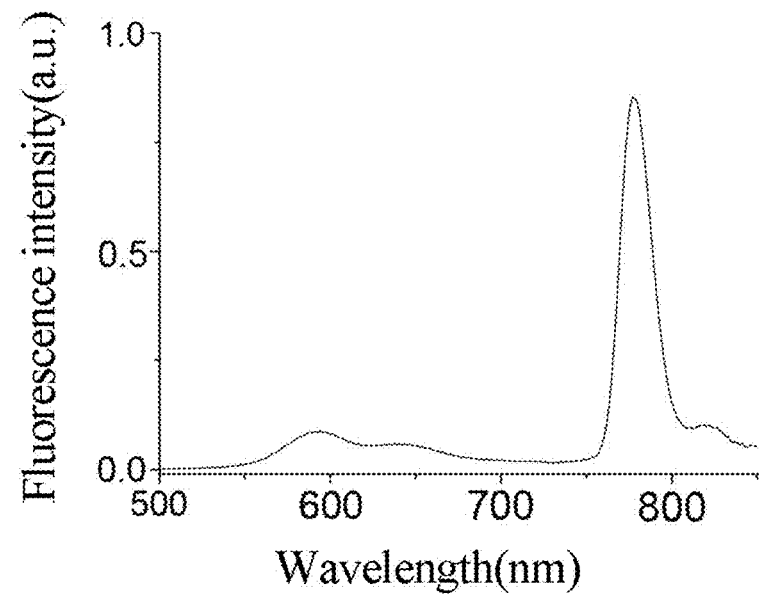
FIG. 8 is a near-infrared fluorescence spectrum showing a hybrid NIR775-MEH-PPV fluorescent conjugated polymer-based nanoprobe.

The results were specifically referred to FIGS. 7-8. It can be seen from FIG. 7 that the hybrid NIR775-PFBT fluorescent conjugated polymer-based nanoprobe had a weak PFBT fluorescence emission at 500-650 nm and a strong NIR775 fluorescence emission peak at 750-800 nm. As shown in FIG. 8, the hybrid NIR775-MEH-PPV fluorescent conjugated polymer-based nanoprobe had a weak MEH-PPV fluorescence emission at 550-700 nm and a strong NIR775 fluorescence emission peak at 750-800 nm. These results indicated that both PFBT and MEH-PPV can react with NIR775 to generate fluorescence resonance energy transfer, which enabled the probe to have an emission peak at the near-infrared region, reducing the interference from the background fluorescence and facilitating the in vivo imaging.

Example 6

In Vitro Photoacoustic Imaging of the Nanoprobe

Different concentrations (31.25, 62.5, 125, 250 and 500 μg/mL) of hybrid NIR775 (0.6 wt %)-PFBT fluorescent conjugated polymer-based nanoprobe solutions were respectively added to five polyvinyl chloride tubes for the photoacoustic imaging with pure water used as a control. The photoacoustic signal intensity and the photoacoustic imaging pictures of respective solutions were both obtained under excitation at 770 nm, where the photoacoustic imaging was performed on a MSOT inVision 128 real-time scanner (iThera Medical Co., Ltd, Germany).

Figure 9:
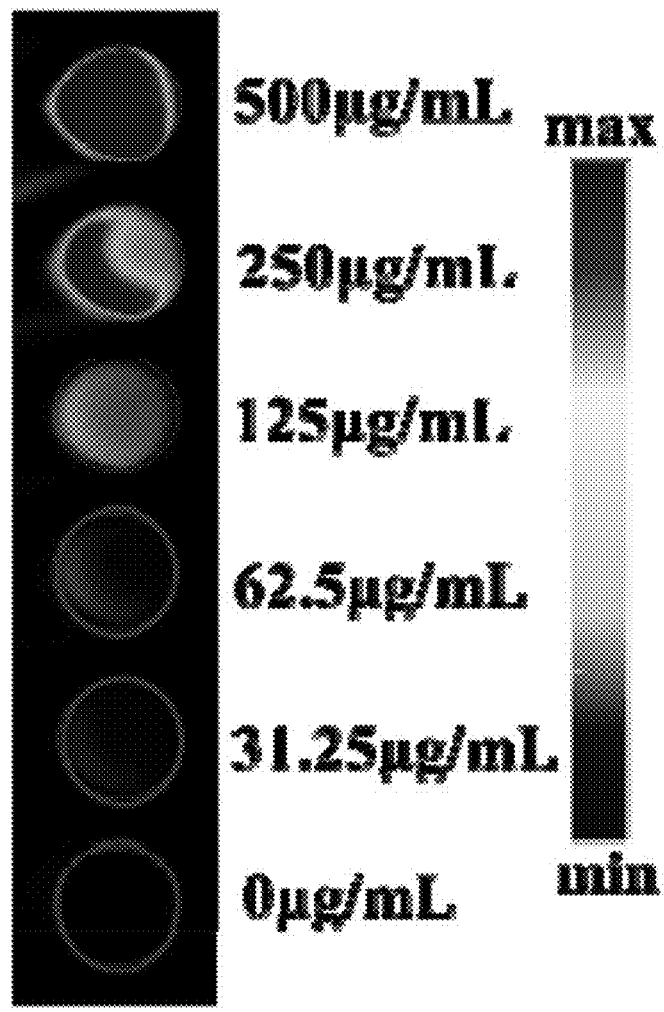
FIG. 9 is an in vitro photoacoustic imaging image showing the hybrid NIR775-PFBT fluorescent conjugated polymer-based nanoprobe.

The results were specifically referred to FIG. 9. As shown in the figure, the intensity of photoacoustic signal was increased with the increase of concentration in the range of 0-500 μg/mL and a significant comparative effect was observed between the photoacoustic imaging pictures of the 500 μg/mL probe solution and pure water (0 μg/mL probe solution). The photoacoustic signal intensity was plotted versus the concentration and in the range of 0-500 μg/mL, the concentration of a sample was linearly correlated with the intensity of the photoacoustic signal with $R^2$ of 0.9992. The results indicated that the hybrid NIR775 fluorescent conjugated polymer-based nanoprobe was suitable for the in vivo photoacoustic imaging.

Example 7

In Vitro $T_1$-Weighted Magnetic Resonance Imaging of the Nanoprobe 20 mL of a sample mixed with the gadolinium-containing magnetic resonance contrast agent (DTPA-BSA (Gd)) was added to a 100K ultrafiltration tube, centrifuged at 4,500 rpm for 3-4 min and serially diluted by 1, 2, 4, 8 and 16 times. 1 mL of the samples with different concentrations were respectively added to several 2 mL EP tubes and then transferred to a medium-size nuclear magnetic resonance analysis and imaging system the samples were tested by a medium sized with magnetic intensity of 0.55 T for detection to collect the MRI cross-sectional images and obtain the $T_1$-weighted images. The $T_1$-weighted imaging was performed on a MesoMR23-060H-I medium-size nuclear magnetic resonance analysis and imaging system (Shanghai Niumag Electronic Technology Co., Ltd), where the resonance frequency was 23.315 MHz; the magnetic intensity was 0.55 T; the coil diameter was 60 mm; and the magnet temperature was 32° C. Other parameters were set as follows: MSE sequence; SFO1 (MHz)=23.315; FOVRead (mm)=80; FOVPhase (mm)=80; TR (ms)=240; TE (ms) =18.2; Slice width (mm)=5; Slices=1; and Average=8.

Figure 10:
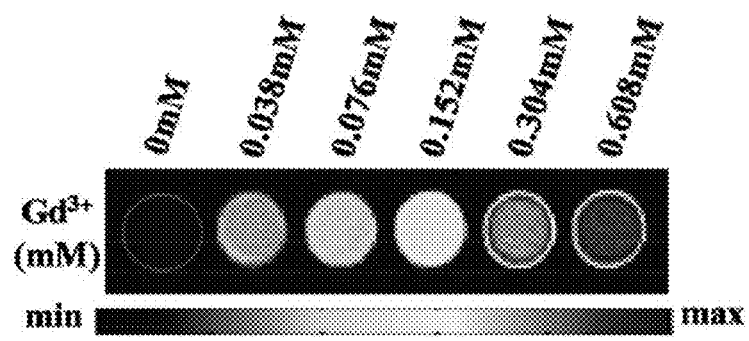
FIG. 10 is an in vitro magnetic resonance image of a hybrid NIR775-Gd$^{3+}$-PFBT fluorescent conjugated polymer-based nanoprobe.

The results were specifically referred to FIG. 10. As shown in the figure, with the increase of the $Gd^{3+}$ concentration, the signal intensity was gradually enhanced and the in vitro $T_1$-weighted imaging showed an obvious regularity. When the $Gd^{3+}$ concentration was 0.608 mM, an obvious contrast was observed between the contrast effects of the probe and water. The results indicated that the hybrid $Gd^{3+}$ fluorescent conjugated polymer-based nanoprobe can be used as a $T_1$ contrast agent in the magnetic resonance imaging.

Example 8

Detection of the Expression Level of Folate Receptor in Tumor Cells

U87MG cells, $SKOV_3$ cells, NCI-H292 cells and HeLa cells at the logarithmic growth phase were respectively digested by pancreatin and prepared into a monodisperse cell suspension. After used for cell counting with a cell counting chamber, respective suspensions were inoculated into a 6-well plate at the same cell density ($1 \times 10^6$ cells/well), and then the cells were cultured in a folate-free 1640 medium with 1% double antibody and 10% serum at 37° C. and 5% $CO_2$ for 12 h. After the cell adhesion was observed, the culture medium was removed and 2 mL of PBS buffer was added. The cells of the experimental group were further added with 5 μL of Mov18 (1:400) and incubated at 37° C. for 30 min to allow the cells to fully bind to the antibody. After that, the cells were washed three times with PBS to remove the unbound antibody, added with 2 mL of PBS buffer, then added with 10 μL of FITC-containing Anti-mouse IgG (1:200), and incubated at 37° C. for 20 min. Finally, the cells were washed three times with PBS, digested and dispersed by 500 μL of PBS. Cells without undergoing the antibody treatment were served as the control group. The cells of both the control group and the experimental group were detected by a flow cytometer and $1 \times 10^4$ cells were collected for analysis, where the excitation wavelength was 488 nm; the receiving wavelength was 515 nm; and the bandwidth was 20 nm. The collected data was analyzed using BD Accuri C6 software.

The results were specifically referred to FIGS. 11A-D. As shown in the figures, the human U87MG glioma cells were folate receptor-negative, while the human $SKOV_3$ ovarian carcinoma cells, human NCI-H292 lung cancer cells (with lymph node metastasis) and human HeLa cervical carcinoma cells were folate receptor-positive. Moreover, the HeLa cells can highly express the folate receptor.

Example 9

Evaluation of Cytotoxicity of the Nanoprobe

A CCK-8 kit was used to evaluate cytotoxicity of the near-infrared fluorescent conjugated polymer-based nanoprobe (taking PFBT NPs as an example), the folic acid-functionalized near-infrared fluorescent conjugated polymer-based nanoprobe (taking FA-PFBT NPs as an example) and the $Gd^{3+}$- and folic acid-functionalized near-infrared fluorescent conjugated polymer-based nanoprobe (taking Gd-FA-PFBT NPs as an example), and the specific steps were described as follows.

The NCI-H292 cells and HeLa cells at the logarithmic growth phase were respectively digested by pancreatin and prepared into monodisperse cell suspensions. After used for cell counting with a cell counting chamber, the cell suspensions were respectively diluted to 50,000 cells/mL, and then 100 μL, of respective cell suspensions were inoculated into a 96-well plate (5×10³ cell/well). 100 μL, of the culture medium without cells was added as the control group, and the 96-well plate was then incubated at 37° C. and 5% $CO_2$ for 12 h.

After the cell adhesion was observed, respective wells containing the cells were sequentially added with 10 μL of each concentration of the nanoprobe solution to be tested to final probe concentrations respectively of 0, 5, 25, 50 and 100 μg/mL, and then the plate was incubated at 37° C. for 24 h. After that, the culture medium in the 96-well plate was removed and the cells were gently washed twice with PBS. Respective wells were added with 110 μL of a pre-prepared mixture of CCK-8 and a culture medium, where a volume ratio of CCK-8 to the culture medium was 1:10. The 96-well plate was then incubated at 37° C. for 2 h. After color change was observed in the culture system, the 96-well plate was transferred to a microplate reader for measurement of OD value at 450 nm. Cell viability was calculated as follows: cell viability*(%)=[A (with nanoprobe)−A (blank)]/[A (0 nanoprobe)−A (blank)]×100%, where A (with nanoprobe) referred to an absorbance of a well containing cells, CCK-8 solution and the probe solution; A (blank) referred to an absorbance of a well containing a medium and the CCK-8 solution but without cells; and A (0 nanoprobe) referred to an absorbance of a well containing cells and the CCK-8 solution but without the probe solution.

Figure 12:
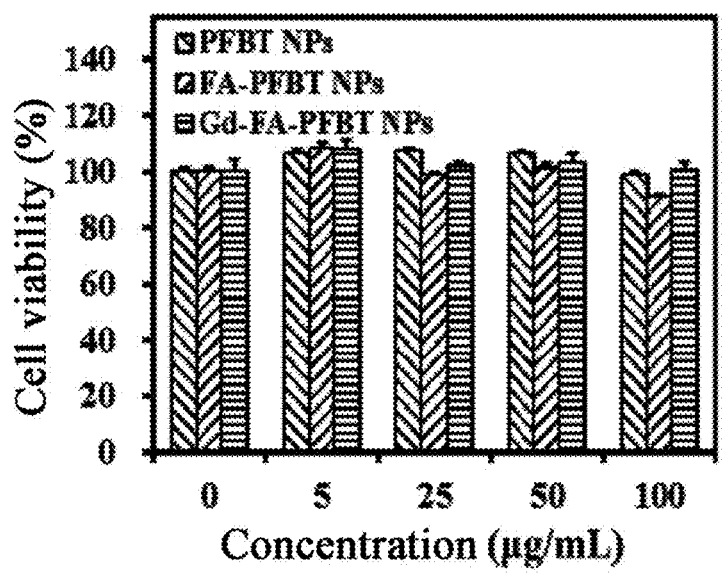
FIG. 12 shows the cytotoxicity of a hybrid fluorescent conjugated polymer-based nanoprobe against NCI-H292.
Figure 13:
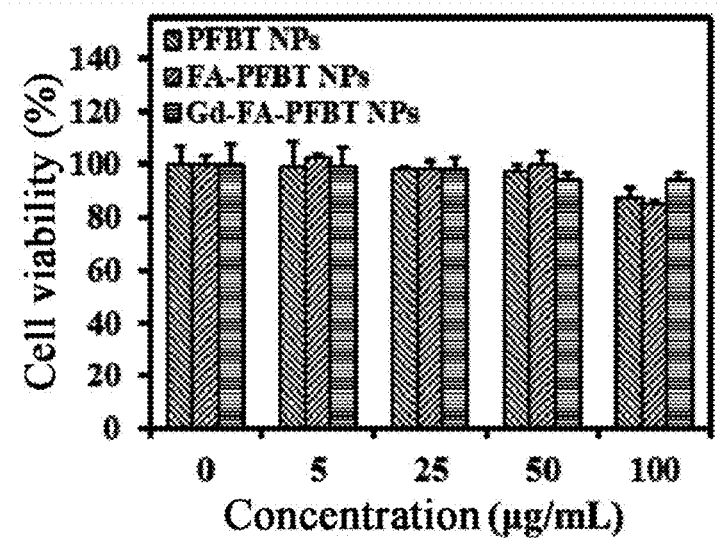
FIG. 13 shows the cytotoxicity of the hybrid fluorescent conjugated polymer-based nanoprobe against HeLa.

The results were specifically referred to FIGS. 12-13. It can be seen from the figures that the viability of NCI-H292 and HeLa cells was respectively greater than 99% and 87% with respect to the unfunctionalized PFBT near-infrared fluorescent polymer-based nanoprobe in the concentration range of 5-100 μg/mL. In the case of a nanoprobe concentration higher than 50 μg/mL, the viability of HeLa cells was significantly reduced ($p<0.05$). For the folate-functionalized near-infrared fluorescent conjugated polymer-based nanoprobe, the viability of NCI-H292 and HeLa cells was respectively greater than 91% and 85%, and significant difference ($p<0.05$) was observed between the viability of the two cells at a nanoprobe concentration of 100 μg/mL. For the $Gd^{3+}$- and folate-functionalized near-infrared fluorescent conjugated polymer-based nanoprobe, the viability of the two types of cells was both reduced by less than 6% even at a concentration of 100 μg/mL. It can be found after the incubation at 37° C. for 24 h that the $Gd^{3+}$- and folate-functionalized near-infrared fluorescent conjugated polymer-based nanoprobe failed to significantly affect the viability of the two types of cells ($p>0.05$) in the range of 5-100 μg/mL. These results indicated that these near-infrared fluorescent conjugated polymer nanoprobes exhibited lower or no cytotoxicity in the concentration range of 5-100 μg/mL.

Example 10

Targeted Imaging of Cells Using the Nanoprobe

NCI-H292 and HeLa cells at the logarithmic growth phase were digested and respectively inoculated to a confocal dish at the same amount (2×10⁴ cells/dish), and after the cell adhesion was observed, the two types of cells were immediately subjected to the cell imaging. The old culture medium was removed, and then 1 mL of serum-free 1640 medium together with 20 μg of PFBT NPs or FA-PFBT NPs was added to the cells. The cells were incubated at 37° C. and 5% $CO_2$ for 24 h. After that, the cells were washed twice with PBS to remove the nanoprobe without undergoing the phagocytosis and fixed with 1 mL of 4% paraformaldehyde solution for 20 min. Then the cells were washed twice again with PBS, covered with a 300 nmol/L DAPI solution and stained in the dark for 30 min. After washed with PBS, the cells were subsequently imaged under a laser scanning confocal microscope.

The parameters of the laser scanning confocal microscope were set as follows: for PFBT, the excitation wavelength was 458 nm and the receiving channel was 520-560 nm; for NIR775, the excitation wavelength was 458 nm and the receiving channel was 750-800 nm; and for DAPI, the excitation wavelength was 405 nm and the receiving channel was 450-480 nm.

Figure 14:
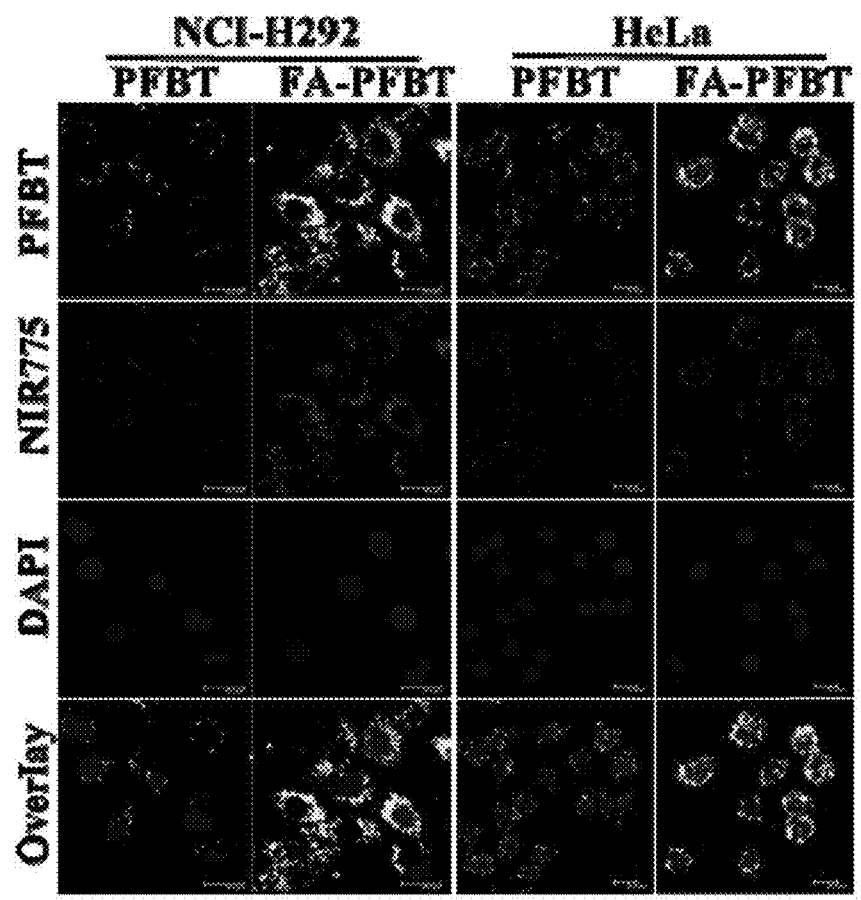
FIG. 14 shows the targeted imaging of NCI-H292 and HeLa cell lines using the hybrid fluorescent conjugated polymer-based nanoprobe.

The results were specifically referred to FIG. 14. It can be seen from the figures that the nanoprobe without the phospholipid folate had a weak intracellular fluorescence signal, while the nanoprobe mixed with the phospholipid folate showed an enhanced intracellular fluorescence signal. Furthermore, the yellow signal of PFBT was substantially overlapped with the red signal of NIR775, and the signal was mainly concentrated in the perinuclear or cytoplasmic early lysosomes. The results indicated that the nanoprobe mixed with the phospholipid folate can target the NCI-H292 and HeLa cells.

Example 11

Flow Cytometric Analysis of the Nanoprobe

Figure 15:
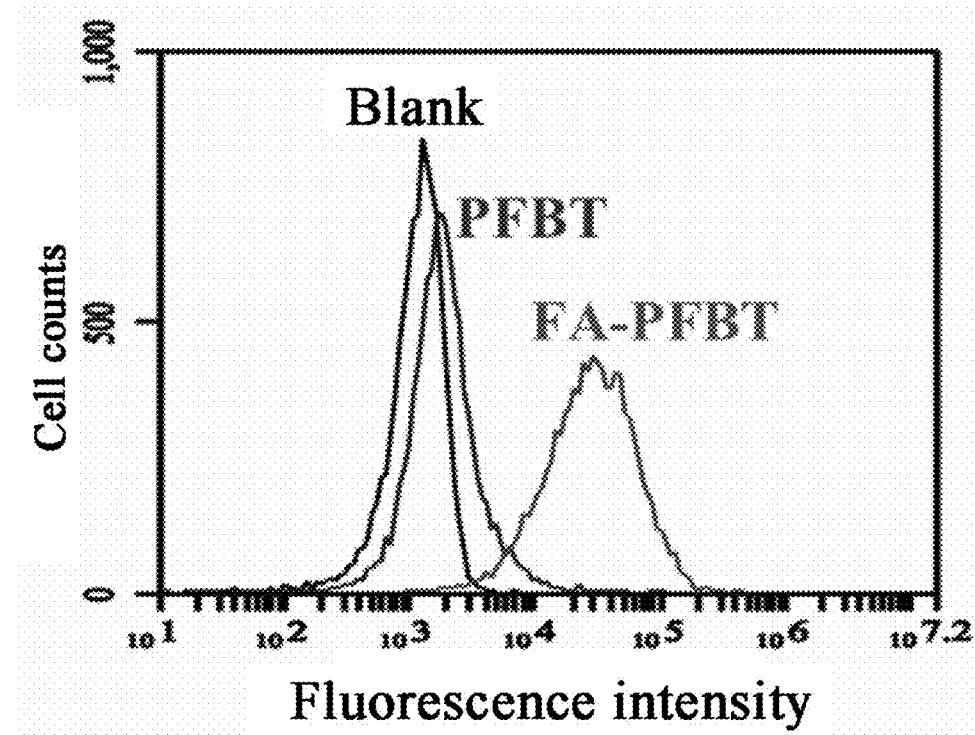
FIG. 15 is a flow cytometry of NCI-H292 mixed with the hybrid fluorescent conjugated polymer-based nanoprobe.
Figure 16:
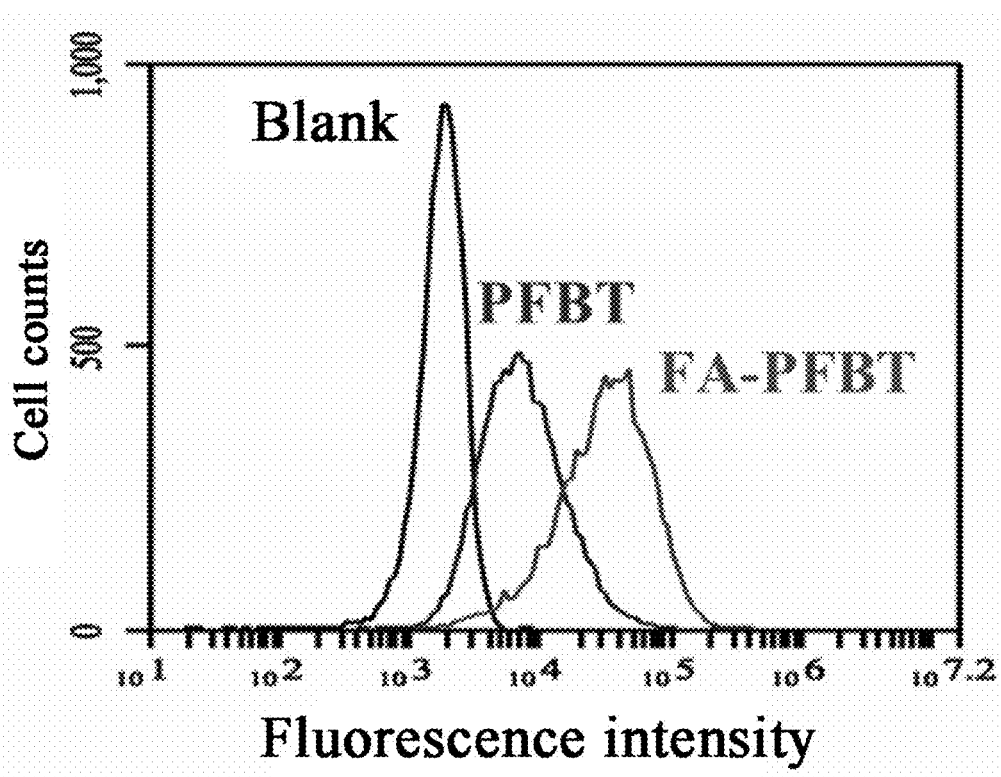
FIG. 16 is a flow cytometry of HeLa mixed with the hybrid fluorescent conjugated polymer-based nanoprobe.

In the flow cytometric analysis, the NCI-H292 and HeLa cells were similarly inoculated to a 6-well cell culture plate (1×10⁶ cells/well), and cultured in a serum-free 1640 medium at 37° C. and 5% $CO_2$ for 12 h. After the cell adhesion was observed, the old culture medium was removed, and then the cells were added with 1 mL of serum-free 1640 medium and respectively added with 20 μg of PFBT fluorescent conjugated polymer-based nanoprobe and 20 μg of the PFBT fluorescent conjugated polymer-based nanoprobe mixed with phospholipid folate. After that the cells were incubated at 37° C. and 5% $CO_2$ for 24 h, washed three times with PBS to remove the free nanoprobes, digested, and dispersed with 500 μL of PBS. 1×10⁴ cells respectively from the control and experimental groups were collected for analysis using a flow cytometer, where the excitation wavelength was 488 nm; the receiving wavelength and bandwidth for PFBT were respectively 515 nm and 20 nm; the NIR775 signal was received through an optical filter; and the obtained data were analyzed using BD Accuri C6 software. The results were specifically referred to FIGS. 15-16. As shown in the figures, after the nanoprobe mixed with the phospholipid folate was used, the corresponding fluorescent signals in the NCI-H292 and HeLa cells were both enhanced, which was in accordance with the results of the confocal cell imaging, demonstrating the targetability of the phospholipid folate to the NCI-H292 and HeLa cells.

Example 12

Detection of Reactive Oxygen in a Nanoprobe Solution 1.25 mg of ADMA powder was added to 2.5 mL of PBS (pH=7.4) and ultrasonicated for 10 min for complete dissolution, and the obtained solution was purple.

1 mL of hybrid NIR775-PFBT near-infrared fluorescent nanoprobe was mixed with 2.5 μL, of the ADMA/PBS solution and then diluted with water to 2.5 mL, where the resulting solution contained 20 μg/mL of Pdots and 5 μg/mL of ADMA.

The mixed solution was irradiated at 460 nm and 100 mW/cm², and the ultraviolet absorption spectrum of the solution was characterized by an ultraviolet spectrophotometer at different intervals until the absorption spectrum of the solution did not change. A pure solution of ADMA (5 μg/mL) without the near-infrared fluorescent nanoprobe was used as the control group and irradiated under the same intensity for the same time.

The PFBT fluorescent polymer-based nanoprobe with a molecular weight of 10,000-20,000 was irradiated every 1 min for a total irradiation time of 12 min. The PFBT fluorescent polymer-based nanoprobe with a molecular weight of 47,000 was irradiated every 1 min from 0 to 10 min and then irradiated every 5 min from 10 to 40 min, and a total irradiation time was 40 min.

Figure 17:
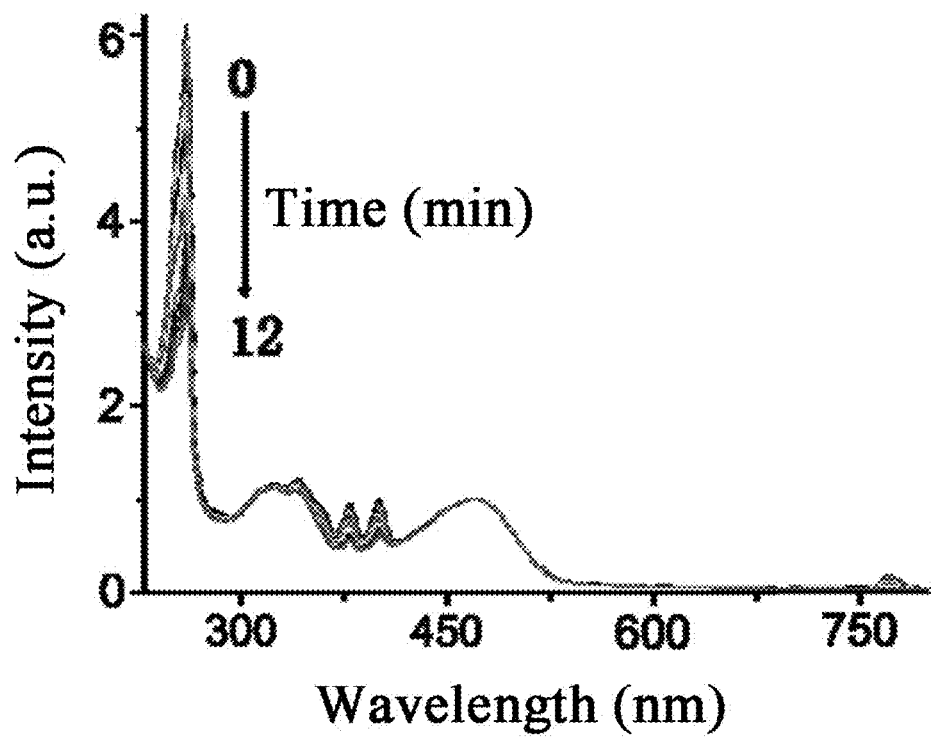
FIG. 17 shows the detection of reactive oxygen generated by a hybrid NIR775-PFBT fluorescent conjugated polymer-based nanoprobe having a molecular weight of 10,000-20,000 in a solution.
Figure 18:
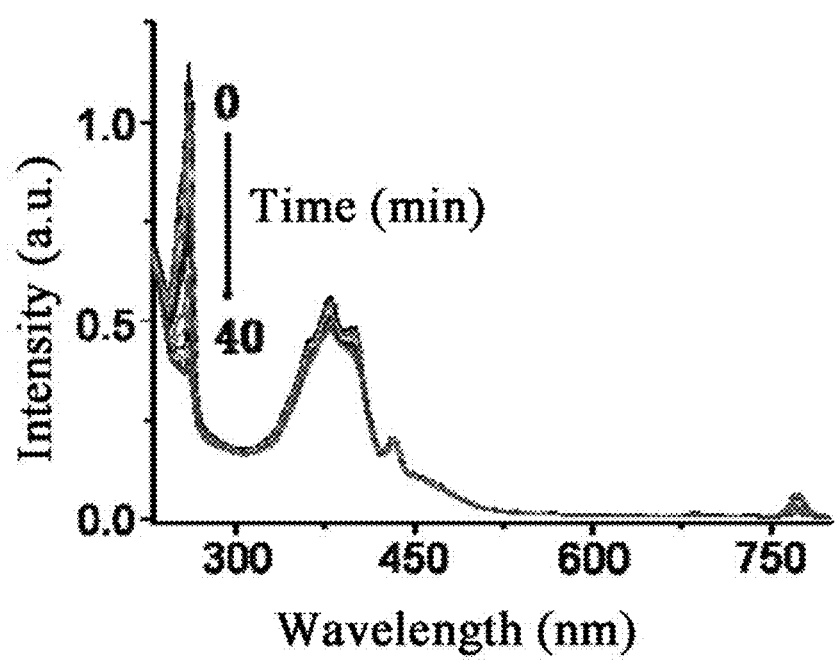
FIG. 18 shows the detection of reactive oxygen generated by a hybrid NIR775-PFBT fluorescent conjugated polymer-based nanoprobe having a molecular weight of 47,000 in a solution.
Figure 19:
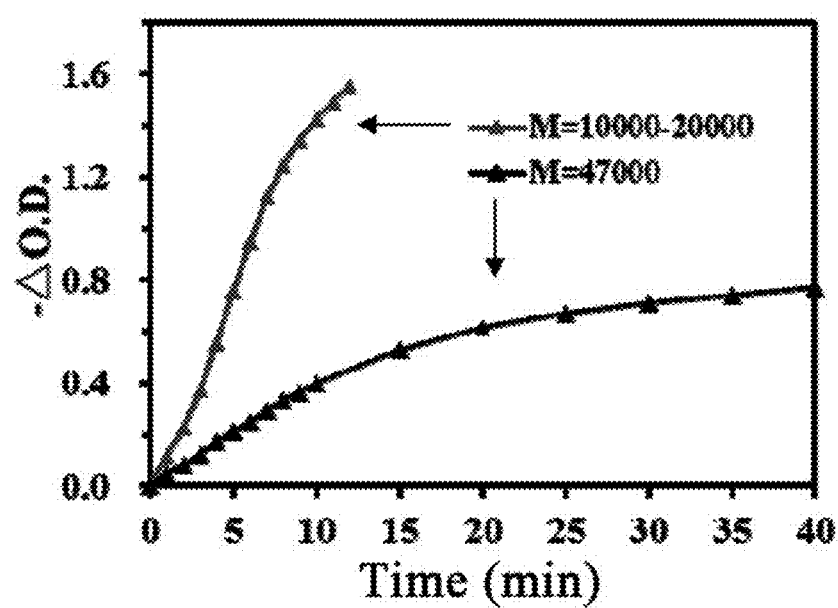
FIG. 19 shows the comparison of generation efficiency of reactive oxygen in a solution between the hybrid NIR775-PFBT fluorescent conjugated polymer-based nanoprobes with different molecular weights.

The results were specifically referred to FIGS. 17-19. As shown in FIG. 17, under the irradiation at 460 nm and 100 mW/cm$^2$, the mixture of the hybrid NIR775-PFBT fluorescent polymer-based nanoprobe with a molecular weight of 10,000-20,000 and ADMA showed a gradual decrease in the ultraviolet absorption intensity at wavelengths around 261 nm, 400 nm and 772 nm with the extension of the irradiation time, and the change was gradually slowed down after 10 min of the irradiation.

As shown in FIG. 18, under the irradiation at 460 nm and 100 mW/cm$^2$, the mixture of the hybrid NIR775-PFBT fluorescent polymer-based nanoprobe with a molecular weight of 47,000 and ADMA showed a gradual decrease in ultraviolet absorption intensity at wavelengths around 261 nm, 400 nm and 772 nm with the extension of the irradiation time, and the change was gradually slowed down after 25 min of the irradiation.

As shown in FIG. 19, in the case of the same irradiation time, the PFBT near-infrared fluorescent nanoprobe with a molecular weight of 10,000-20,000 showed a greater change in the ultraviolet absorption intensity at 261 nm when compared to the PFBT near-infrared fluorescent nanoprobe with a molecular weight of 47,000. Moreover, it was only required 10 min for the PFBT near-infrared fluorescent nanoprobe with a molecular weight of 10,000-20,000 to reach the maximum ultraviolet absorption intensity at 261 nm, while for the PFBT near-infrared fluorescent nanoprobe with a molecular weight of 47,000, 25 min were required. This indicated that the compared to the PFBT near-infrared fluorescent nanoprobe with a molecular weight of 47,000, the PFBT near-infrared fluorescent nanoprobe with a molecular weight of 10,000-20,000 can generate the singlet oxygen at a larger amount and a higher efficiency.

Example 13

Detection of Singlet Oxygen Generated by the Nanoprobe in the Cells and Detection of Apoptosis The NCI-H292 and HeLa cells at the logarithmic growth phase were harvested at the same amount, digested and inoculated into a confocal dish (4×10$^4$ cells/dish). Then the cells were cultured in a serum-containing 1640 medium. After the cell adhesion was observed, the old culture medium was removed, and the cells were added with 1 mL of fresh serum-free 1640 medium together with 0 or 20 μg of a hybrid phospholipid folate-PFBT near-infrared fluorescent nanoprobe (having a molecular weight 10,000-20,000) and cultured at 37° C. and 5% $CO_2$ for 24 h. After that, the culture solution was removed, and the cells were washed three times with PBS to remove the nanoparticles without undergoing phagocytosis and added with 1 mL of fresh serum-free 1640 medium. A LED light source with a wavelength of 460 nm and a power of 50 mW/cm$^2$ was used to continuously irradiate the cells for 20 min, where the cells mixed with the nanoprobe and undergoing the irradiation were used as the experimental group; and the cells mixed with the nanoprobe but without undergoing the irradiation were used as the control group together with the cells undergoing the irradiation for 20 min but without addition of the nanoprobe.

The intracellular singlet oxygen was detected as follows. 3.5 mg of DCFH-DA was dissolved in 721 μL of 10 mM ethanol, diluted to 1.0 mM with a serum-free culture medium. This 1.0 mM solution was further diluted to 10 mM with the serum-free culture medium for use. The irradiated cells were stained with the 10 μM DCFH-DA solution in the dark for 20 min, gently washed three times with PBS and transferred to a laser scanning confocal microscope for imaging, where the DCFH-DA was excited at 488 nm and the receiving channel was set at 510-520 nm.

The detection of apoptosis was performed as follows. 1 mg of PI was dissolved in 10 mL of PBS to obtain a 100 μg/mL PI solution, and 1 mL of the 100 μg/mL PI solution was added to 50 mL PBS to obtain a 2 μg/mL PI solution for use. The irradiated cells were stained with the 2 μg/mL PI solution in the dark for 20 min, gently washed three times with PBS and transferred to a laser scanning confocal microscope for imaging. The PI was excited at 561 nm and the receiving channel was set at 600-630 nm.

Figure 20:
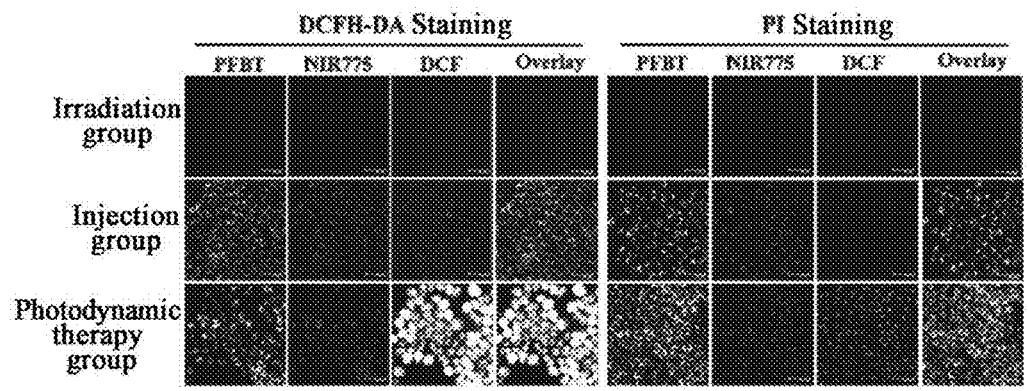
FIG. 20 shows the detection of reactive oxygen and apoptosis in NCI-H292 cell line in the use of the hybrid fluorescent conjugated polymer-based nanoprobe.
Figure 21:
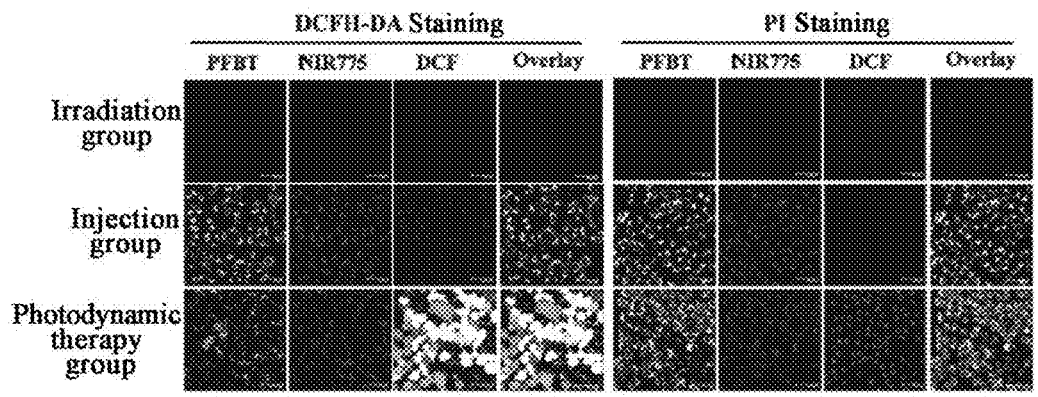
FIG. 21 shows the detection of reactive oxygen and apoptosis in HeLa cell line in the use of the hybrid fluorescent conjugated polymer-based nanoprobe.

The results were specifically referred to FIGS. 20-21. When taken up by cells, the DCFH-DA was converted into non-fluorescent DCFH, and in the case of the presence of singlet oxygen in the cells, the non-fluorescent DCFH was oxidized into the highly-fluorescent DCF. Whether there was singlet oxygen in the cells can be determined by detecting the signal of DCF. PI dye can pass through the cell membrane and stain the nuclei of damaged cells, while the nuclei of living cells cannot be stained. Therefore, the singlet oxygen in cells can be detected through the DCFH-DA and the apoptosis can be detected using the PI dye. It can be seen from the figures that neither the signal of DCF nor the signal of PI was detected in NCI-H292 and HeLa cells from the group undergoing irradiation for 20 min but without undergoing the co-incubation with nanoprobe or the group undergoing the co-incubation with nanoprobe but without irradiation. While for the NCI-H292 and HeLa cells from the group undergoing both the co-incubation with nanoprobe and the irradiation for 20 min, significant DCF green fluorescence signals and PI red signals were both detected. This indicated that singlet oxygen was generated in the cells co-incubated with nanoprobe under irradiation, and then the singlet oxygen can damage the cells to cause apoptosis. In addition, the signals of PFBT and NIR775 corresponding to the nanoprobe were also observed in the cells co-incubated with nanoprobe, demonstrating the targetability of the nanoprobe.

Example 14

Detection of Photodynamic Toxicity of the Nanoprobe in Cells

The killing effect of the nanoprobe on NCI-H292 and HeLa cells under the irradiation at 460 nm was investigated using a CCK-8 kit, which was specifically described as follows.

NCI-H292 and HeLa cells at the logarithmic growth phase were respectively digested by pancreatin and prepared into the monodisperse cell suspensions. After counted using a cell counting chamber, the monodisperse cell suspensions were respectively diluted to 50,000 cells/mL, and then 100 μL of respective cell suspensions were inoculated into a 96-well plate (5×10$^3$ cells/well). 100 μL of the culture medium without cells was added as the control group, and the 96-well plate was incubated at 37° C. and 5% $CO_2$ for 12 h.

After the cell adhesion was observed, in order to promote the phagocytosis of the cells to the hybrid phospholipid folate-PFBT (having a molecular weight of 10,000-20,000) near-infrared fluorescent nanoprobe to enhance the photodynamic effect, the old medium was replaced by a serum-free 1640 medium, and then respective wells containing cells were sequentially added with 10 μL of each concentration of the nanoprobe solutions to be tested to achieve the final probe concentrations of 0, 0.5, 1, 2.5, and 5 μg/mL, respectively. The 96-well plate was incubated at 37° C. for 24 h. After that, the old medium was removed and the cells were gently washed twice with PBS to remove the nanoprobe that was not phagocytized by the cells, and added with 100 μL of a fresh medium. The cells were irradiated under a LED light source with a power of 50 mW/cm$^2$ and a wavelength of 460 nm respectively for 0, 10, 20 and 30 min. After the irradiation, the cells in respective wells were added with 10 μL of CCK-8 solution and incubated at 37° C. for 2 h. After a color change was observed, the 96-well plate was transferred to a microplate reader for the measurement of OD value at 450 nm. The killing effect of different concentrations of nanoprobes on NCI-H292 and HeLa cells at different irradiation times was calculated by the following formula.

The cell viability was calculated as follows: cell viability* (%)=[A (with nanoprobe)-A (blank)HA (0 nanoprobe)-A (blank)]×100%, where A (with nanoprobe) referred to an absorbance of the well containing cells, a CCK-8 solution and a probe solution; and A (blank) referred to an absorbance of a well containing a medium and a CCK-8 solution but without cells; and A (0 nanoprobe) referred to an absorbance of a well containing cells and a CCK-8 solution but without the probe solution.

Figure 22:
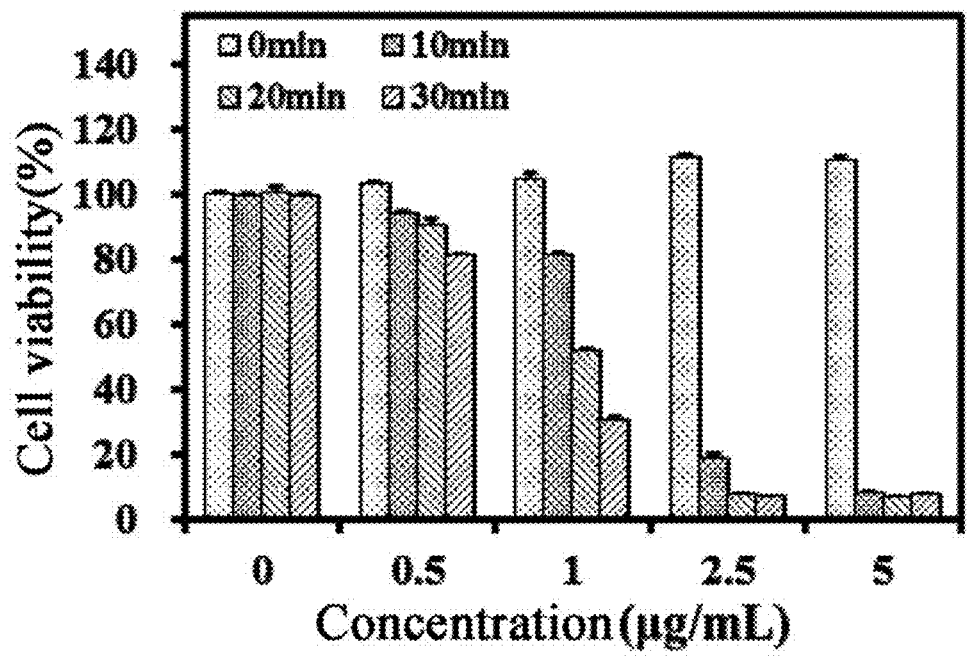
FIG. 22 shows the photodynamic toxicity of the hybrid fluorescent conjugated polymer-based nanoprobe against NCI-H292 cell line.
Figure 23:
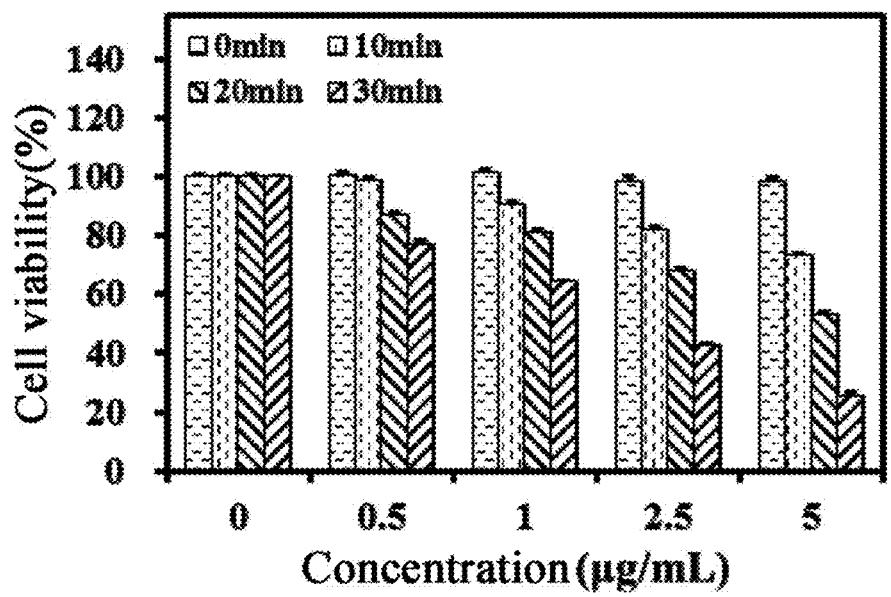
FIG. 23 shows the photodynamic toxicity of the hybrid fluorescent conjugated polymer-based nanoprobe HeLa against cell line.

The results were specifically referred to FIGS. 22-23. As shown in the figures, in the case of the same irradiation dose, the viability of the two types of cells was gradually decreased as the concentration increased from 0 to 5 μg/mL, while the cells without undergoing the irradiation showed negligible cytotoxicity. For the same concentration of nanoprobes, the cell viability decreased with the extension of the irradiation time. When the concentration and irradiation dose reached a certain value, there was a significant decrease in cell viability of the two types of cells ($p<0.05$). In the case of a concentration of 2.5 μg/mL and an irradiation dose of 60 J/cm$^2$, more than 90% of the NCI-H292 cells were killed. Further, at an irradiation dose of 90 J/cm$^2$, the IC50 values (semi-lethal concentration) of NCI-H292 and HeLa cells respectively were 0.8 μg/mL and 2.43 μg/mL.

Example 15

Photodynamic Therapy of Subcutaneous Tumor Using the Nanoprobe

Mice axillarily inoculated with NCI-H292 tumor were selected to study the photodynamic therapy effect of a hybrid phospholipid folate-PFBT (with a molecular weight of 10,000-20,000) near-infrared fluorescent nanoprobe on the mouse subcutaneous tumor. After the tumors of the mice grew to a volume of about 100-150 mm$^3$, 15 nude mice were randomly divided into three groups (5 in each group), where the first group was the irradiation group, in which the mice were irradiated but not subjected to the injection of the probe; the second group was the injection group, in which the mice were treated by tail vein injection of the nanoprobe but not irradiated; and the third group was the photodynamic group, in which the mice were treated not only by tail vein injection of the nanoprobe but also by irradiation. For the mice required the tail vein injection of the nanoprobe, the injection was performed every seven days and 40 μg of the nanoprobe for each injection. For the mice requiring irradiation, a LED with a wavelength of 460 nm and a power of 100 mW/cm$^2$ was used as the light source to irradiate the mice at the tumor site for 30 min each time. For the photodynamic group, the mice were irradiated immediately after the injection of the nanoprobe. The irradiation for the photodynamic group and the irradiation group was performed every 7 days, and the treatment time was 28 days in total.

The size and weight of the mouse tumors were measured and recorded every 7 days, where the volume of the tumor was calculated according to the following formula: tumor volume=(tumor length)×(tumor width)$^2$/2, and the relative volume of the tumor was calculated as $V/V_0$ ($V_0$ was the volume of the initial tumor). After the treatment on the 28th day, all of the experimental mice were euthanized, and their tumors, hearts, livers, spleens, lungs and kidneys were collected, stored in 4% paraformaldehyde, and then stained by HE to observe whether a damage occurred to the tumor site and whether the nanoprobe was toxic to various tissues.

Figure 24:
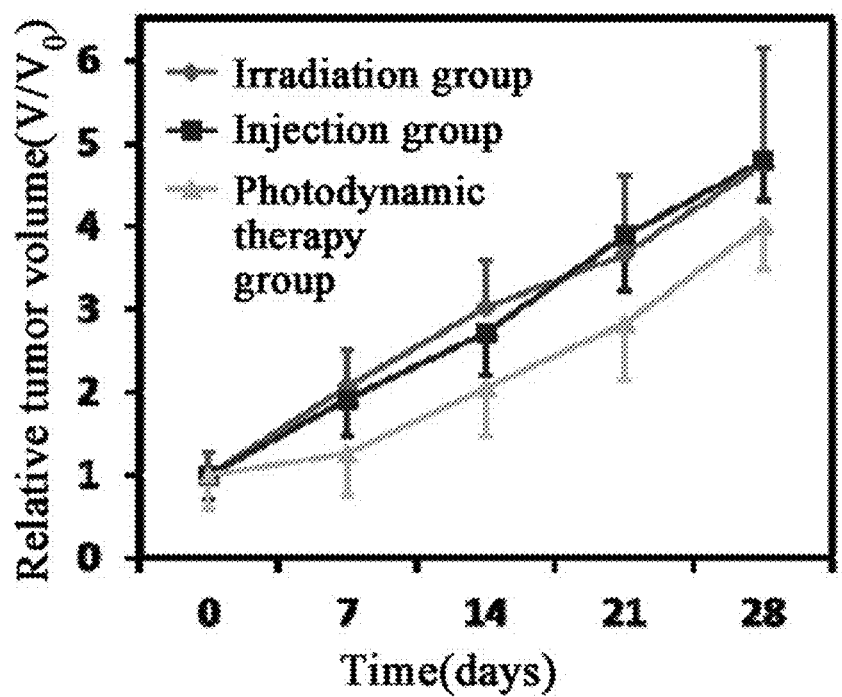
FIG. 24 shows a growth curve of NCI-H292 tumor in the in vivo photodynamic therapy using the hybrid fluorescent conjugated polymer-based nanoprobe.
Figure 25:
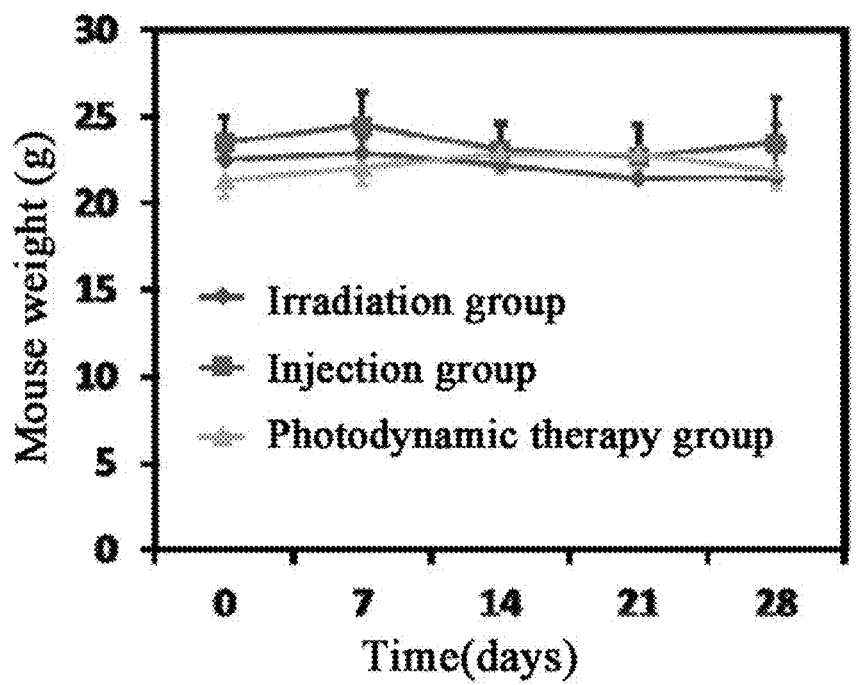
FIG. 25 shows the weight change of mouse with NCI-H292 tumor in the in vivo photodynamic therapy using the hybrid fluorescent conjugated polymer-based nanoprobe.
Figure 29:
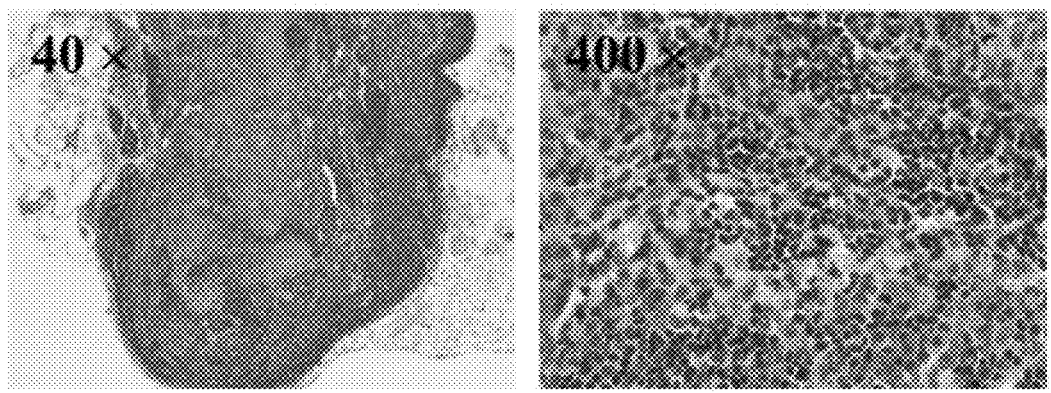
FIG. 29 shows the H & E staining of AX lymph nodes with NCI-H292 tumor metastasis.
Figure 30:
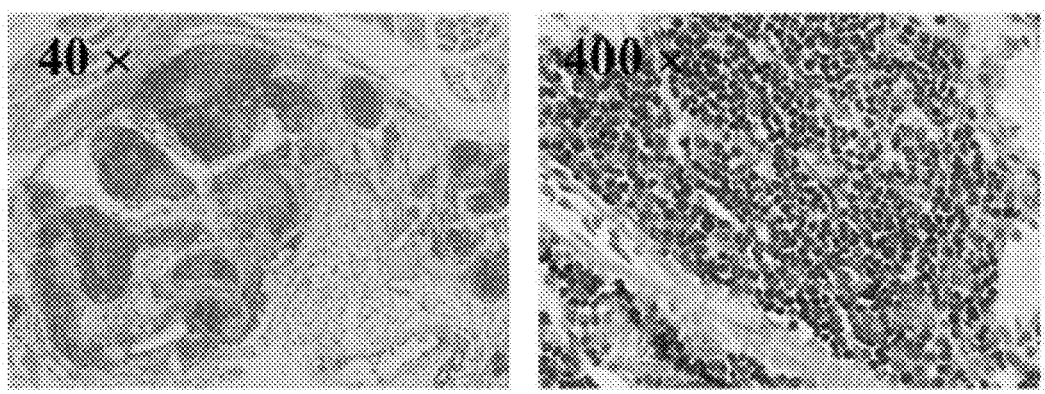
FIG. 30 shows the H & E staining of PO lymph nodes with NCI-H292 tumor metastasis.
Figure 31:
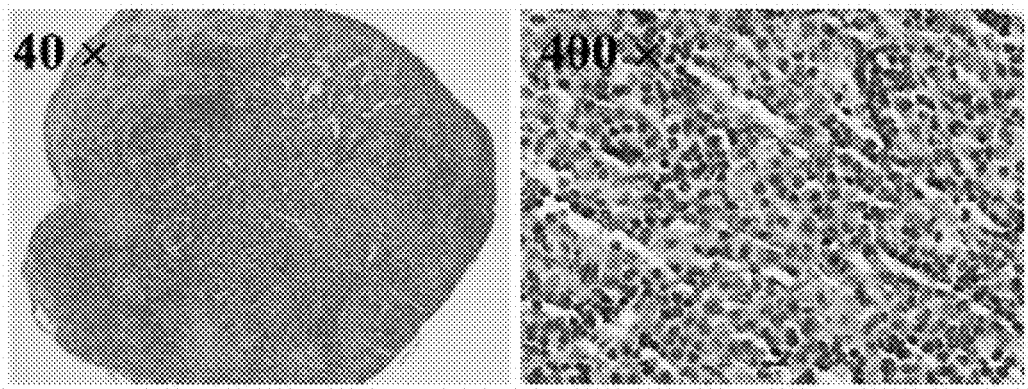
FIG. 31 shows the H & E staining of SC lymph nodes with NCI-H292 tumor metastasis.
Figure 32:
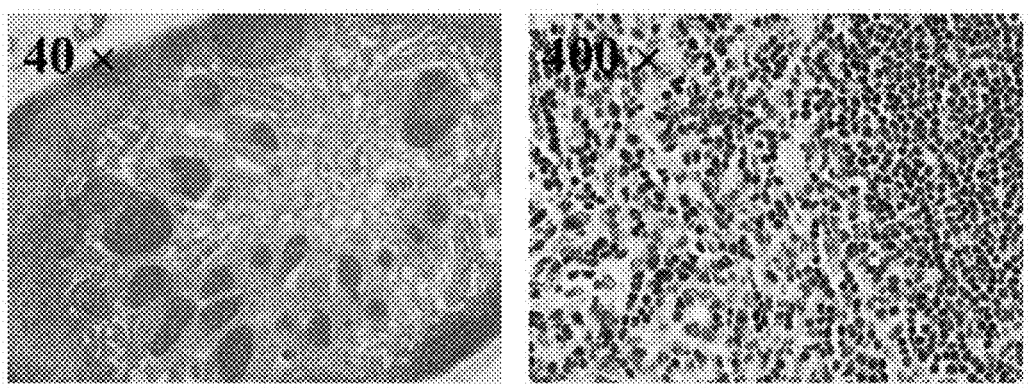
FIG. 32 shows the H & E staining of IN lymph nodes with NCI-H292 tumor metastasis.
Figure 33:
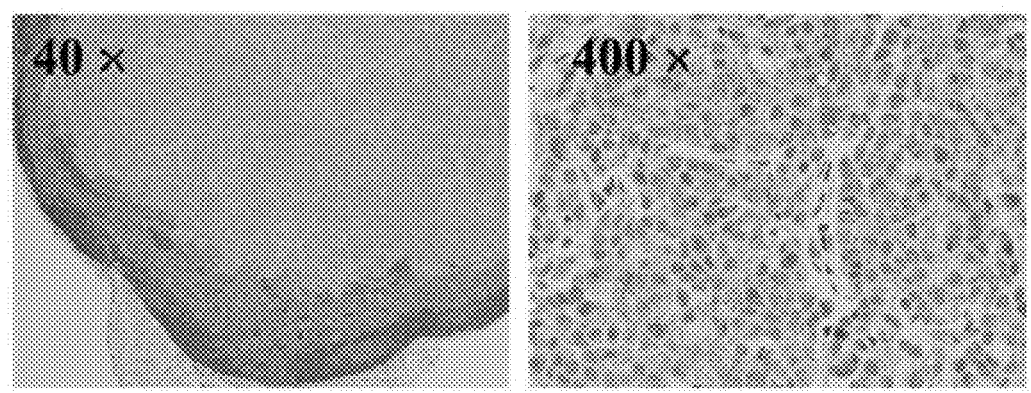
FIG. 33 shows the VEGF staining of AX lymph nodes with NCI-H292 tumor metastasis.
Figure 34:
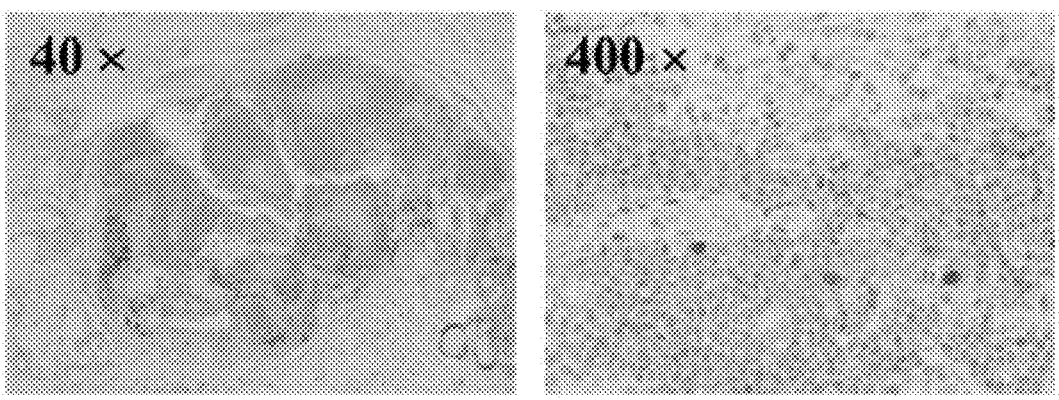
FIG. 34 shows the VEGF staining of PO lymph nodes with NCI-H292 tumor metastasis.
Figure 35:
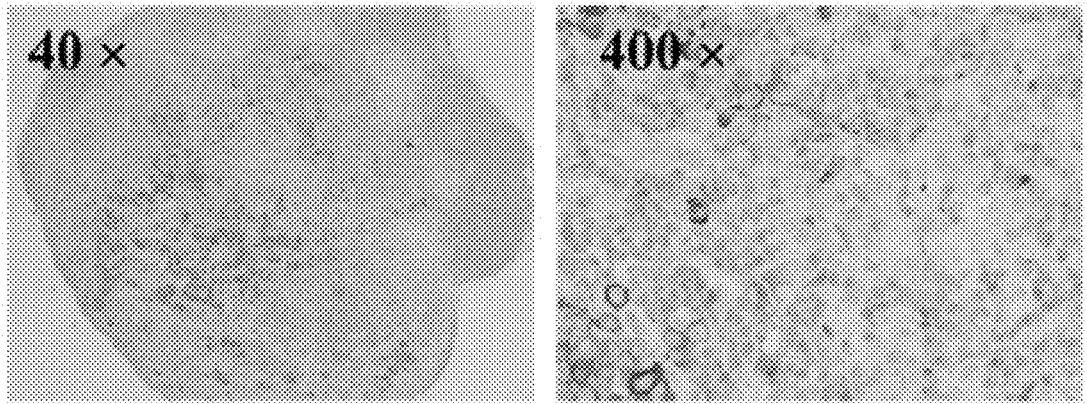
FIG. 35 shows the VEGF staining of SC lymph nodes with NCI-H292 tumor metastasis.
Figure 36:
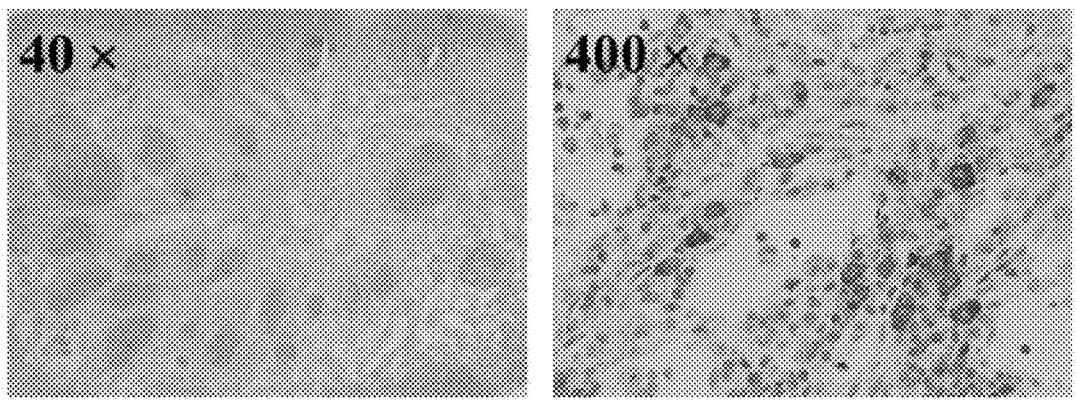
FIG. 36 shows the VEGF staining of IN lymph nodes with NCI-H292 tumor metastasis.

The results were specifically referred to FIGS. 24-26. As shown in FIG. 24, compared to the irradiation group and the injection group, the tumor growth of the mice in the photodynamic group was inhibited after the treatment. These results indicated that the hybrid NIR775-PFBT fluorescent polymer-based nanoprobe can significantly inhibit the tumor under irradiation. As shown in FIG. 25, in the different treatment processes, the weight of the mice was fluctuated within the normal range and no obvious abnormalities were observed, which indicated that the nanoprobe and the irradiation dose used in the experiment were not significantly toxic to mice. As show in FIG. 26, compared to the irradiation group and the injection group, most of the corresponding tumor cells in the photodynamic group were round, in which deepened nucleus staining, concentrated cytoplasm and agglomerate chromatin were observed, which indicated that more apoptosis and necrosis occurred to the tumor cells in the photodynamic group. These results demonstrated the inhibitory effect of the photodynamic therapy on the tumor growth. In addition, no significant histological and morphological change were observed in the hearts, livers, spleens, lungs and kidneys of the mice in all treatment groups, indicating that the fluorescent polymer-based nanoprobe had less or no toxicity to mice.

Example 16

Research on a Lymphatic Metastasis Tumor Model in Nude Mice

The axillary lymph node (AX) metastasis model was established as follows. The tumor cells in the logarithmic growth phase were harvested, digested, centrifuged and dispersed in PBS to prepare a cell suspension having a certain concentration. 200 μL of the tumor cell suspension (2×10$^6$ cells) was subcutaneously inoculated to the axillary site of each mouse, and the tumor was observed after about 10 days.

The popliteal lymph node (PO) metastasis model was established as follows. The tumor cells in the logarithmic growth phase were harvested, digested, centrifuged and dispersed in PBS to prepare a cell suspension having a certain concentration. 40 μL of the tumor cell suspension ($2\times10^6$ cells) was subcutaneously inoculated to the pad of the hind leg of each mouse, and the tumor was observed after about 10 days.

In order to validate the lymph node metastasis model, the tumor tissue, axillary lymph node (AX), popliteal lymph node (PO), sciatic lymph node (SC) and inguinal lymph node (IN) were fixed for paraffin embedding, HE staining and Anti-VEGFA antibody (ab46154) staining. Then the tissue sections were imaged under an optical microscope.

The results were specifically referred to FIGS. 27-36. As shown in the figures, metastatic tumor cells were detected in the axillary lymph node AX (a sentinel lymph node) of the mice axillarily inoculated with the NCI-H292 tumor; while for the mice inoculated with NCI-H292 tumor at the pad, metastatic tumor cells were detected in the popliteal lymph node PO (a sentinel lymph node), the sciatic lymph node SC (a secondary lymph node) and the inguinal lymph node IN. The results demonstrated the validity of the lymphatic metastasis tumor model.

Example 17

Fluorescence Imaging of the Nanoprobe

When the NCI-H292 tumor at the pad reached a diameter of 5-8 mm, the hybrid phospholipid folic acid-PFBT near-infrared fluorescent conjugated polymer-based nanoprobe was simultaneously injected into the two pads of the mouse to observe the targeting effect of the nanoprobe to the metastatic lymph node. The mice were in vivo imaged using the PerkinElmer's IVIS Lumina XRMS Series III imaging system, where the excitation light source had a wavelength of 460 nm and a 780 nm optical filter was used in the receiving channel.

Figure 37:
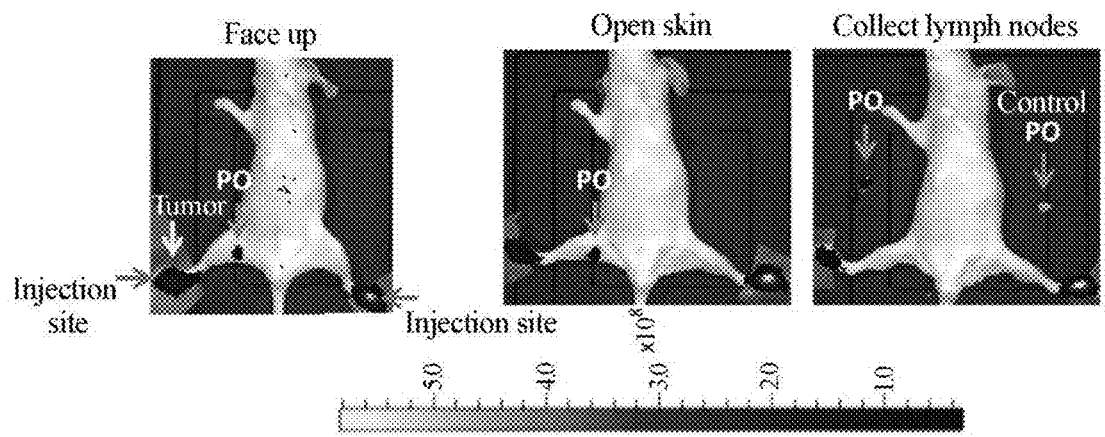
FIG. 37 shows the in vivo near-infrared fluorescence imaging (in a NCI-H292 tumor model) of lymph node metastasis using the hybrid fluorescent conjugated polymer-based nanoprobe (7.5 μg).
Figure 38:
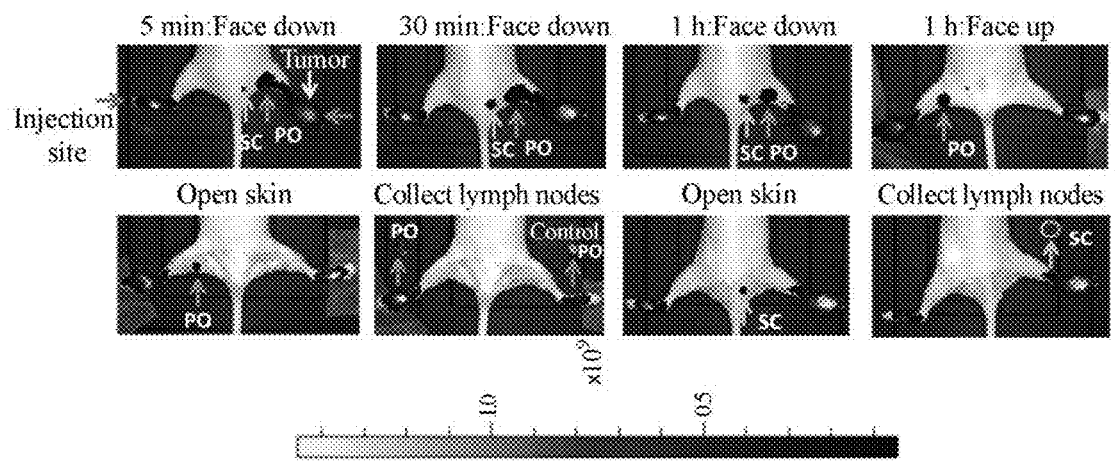
FIG. 38 shows the in vivo near-infrared fluorescence imaging (in a NCI-H292 tumor model) of lymph node metastasis using the hybrid fluorescent conjugated polymer-based nanoprobe (15 μg).
Figure 39:
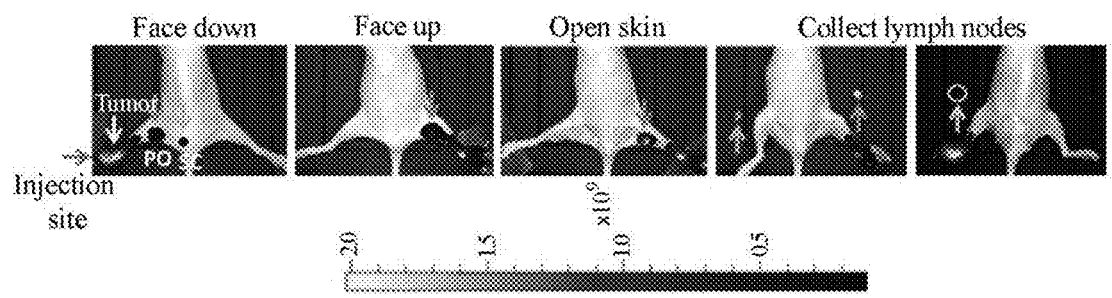
FIG. 39 shows the in vivo near-infrared fluorescence imaging (in a NCI-H292 tumor model) of lymph node metastasis using the hybrid fluorescent conjugated polymer-based nanoprobe (170 μg).

The results were specifically referred to FIGS. 37-39. As shown in FIG. 37, after 2 h of the injection of the near-infrared fluorescent conjugated polymer-based nanoprobe to the mouse through the pad (the injection was performed when the tumor grew to a diameter of 5 mm), a near-infrared signal emitted by the probe was detected in the popliteal lymph node PO at one side of the tumor, but no probe signal was found in another PO at the opposite side of the tumor. When the skin of the mouse was incised and two POs were taken out, it was confirmed that the near-infrared fluorescent signal of the probe was only detected in one PO. The results demonstrated that the nanoprobe can specifically and targetedly image the PO lymph node where the tumor metastasis occurred. As shown in FIG. 38, the near-infrared signal of the probe was detected both in the popliteal lymph node PO and the sciatic lymph node SC at one side of the tumor after different times of the injection of the near-infrared fluorescent conjugated polymer-based nanoprobe through the pad (the injection was performed when the tumor grew to a diameter of about 8 mm), but no probe signal was observed in the PO and SC at the opposite side of the tumor. When the skin of the mouse was incised and the lymph nodes were taken out, it was confirmed that the near-infrared fluorescent signal of the probe was only detected in the PO and SC at one side of the tumor. The results indicated that the nanoprobe can specifically and targetedly image the PO and SC lymph nodes where the tumor metastasis occurred. As shown in FIG. 39, after 20 days of injection of the near-infrared fluorescent conjugated polymer-based nanoprobe through the pad (the injection was performed when the tumor grew to a diameter of about 8 mm), the fluorescent signal of the probe can still be detected in the popliteal lymph node PO and sciatic lymph node SC at one side of the tumor. This result indicated that this nanoprobe can be retained in the lymph node for a long time.

Example 18

Photoacoustic Imaging of the Nanoprobe

When the NCI-H292 tumor at the pad reached a diameter of 5-8 mm, the hybrid phospholipid folic acid-PFBT near-infrared fluorescent conjugated polymer-based nanoprobe was simultaneously injected into the two pads of the mouse to observe the targeting effect of the nanoprobe to the lymph node metastasis. The in vivo photoacoustic imaging for a small animal was performed on a MSOT inVision 128 real-time scanner (iThera Medical Co., Ltd, Germany), where the excitation waveband was 680-800 nm; an excitation peak was selected every 10 nm; and the scanning stepsize was 0.2 mm. The data obtained at the optimal excitation wavelength of 770 nm was selected and used for the image reconstruction based on the back-projection algorithm.

Figure 40:
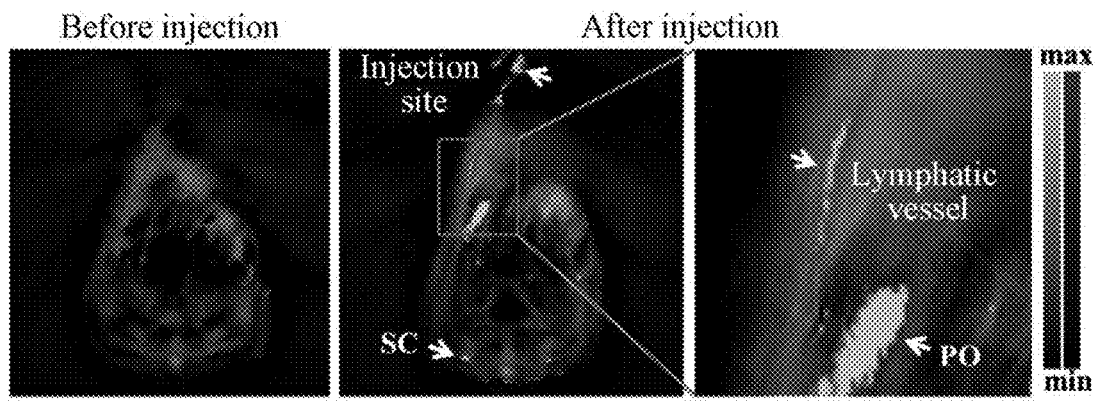
FIG. 40 shows the in vivo photoacoustic imaging of lymph node metastasis using the hybrid fluorescent conjugated polymer-based nanoprobe, where red indicates a photoacoustic signal of $HbO_2$ and green indicates a photoacoustic signal of the nanoprobe (in a NCI-H292 tumor model).
Figure 41:
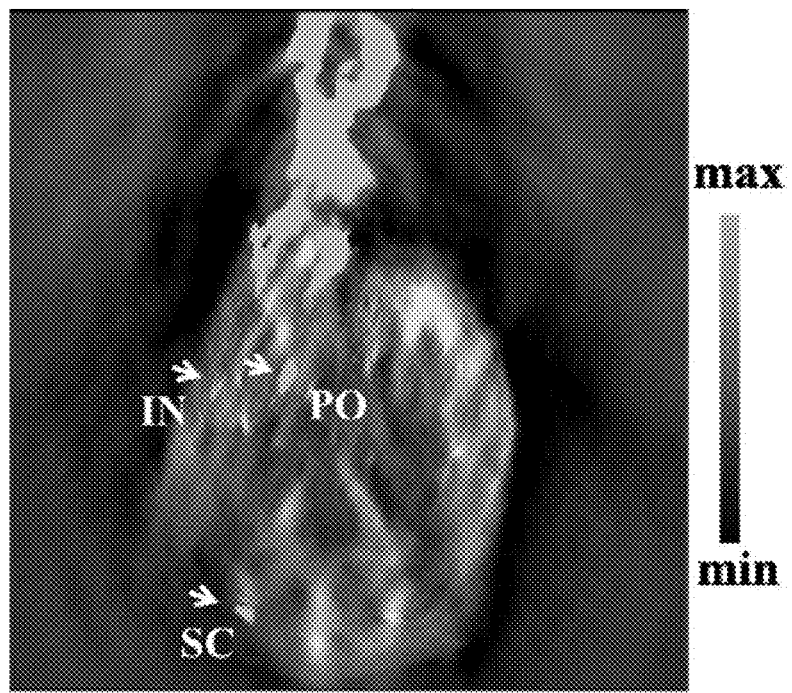
FIG. 41 shows the in vivo photoacoustic imaging of lymph node metastasis using the hybrid fluorescent conjugated polymer-based nanoprobe, where green indicates the photoacoustic signal of the nanoprobe (in a NCI-H292 tumor model).

The results were specifically referred to FIGS. 40-41. As shown in FIG. 40, after the near-infrared fluorescent polymer-based nanoprobe was injected through the pad, the photoacoustic signal of the nanoprobe was observed in the popliteal lymph node PO, the sciatic lymph node SC and lymphatic vessel. As shown in FIG. 41, after 4 h of the injection, the photoacoustic signal of the nanoprobe was detected in the popliteal lymph node PO, the sciatic lymph node SC and the inguinal lymph node IN.

Example 19

Magnetic Resonance Imaging and the Near-Infrared Fluorescence Imaging of the Nanoprobe The mice were scanned in a $T_1$-weighted imaging mode using a 7.05 T MRI system (Biospec System 70/20, Brucker, Ettlingen, Germany) with a coil diameter of 40 mm. The mice with NCI-H292 tumor at the pad were injected with a near-infrared fluorescent conjugated polymer-based nanoprobe simultaneously mixed with a gadolinium-containing magnetic resonance contrast agent DTPA-BSA (Gd) and a phospholipid folic acid through the pad, where the magnetic resonance signal was scanned respectively before and after the injection of the probe. The scanning parameters were set as follows: TE=6 ms; TR=1500 ms; Flip Angle=90 deg; Slice Thickness=1 mm; Field=7.05 T; and DFOV=25 mm. The MRI image exportation and the data analysis were both performed using the ImageJ software. After the MRI, the experimental mice were further scanned using the fluorescence imaging system to verify the signal distribution of the nanoprobe, where the fluorescence imaging was performed using PerkinElmer's IVIS Lumina XRMS Series III imaging system; the excitation wavelength was 460 nm; and a 780 nm optical filter was in the receiving channel.

Figure 42:
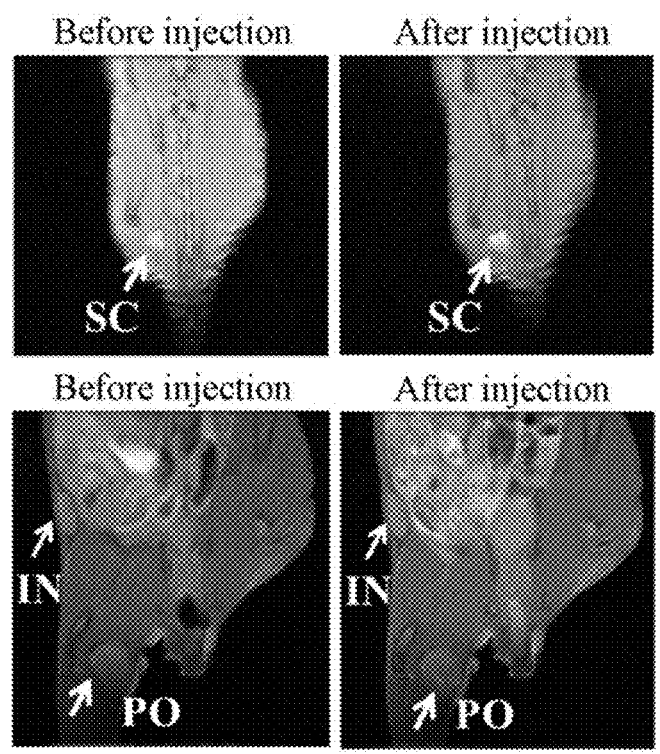
FIG. 42 shows the in vivo magnetic resonance imaging of lymph node metastasis using the hybrid fluorescent conjugated polymer-based nanoprobe (in a NCI-H292 tumor model).
Figure 43:
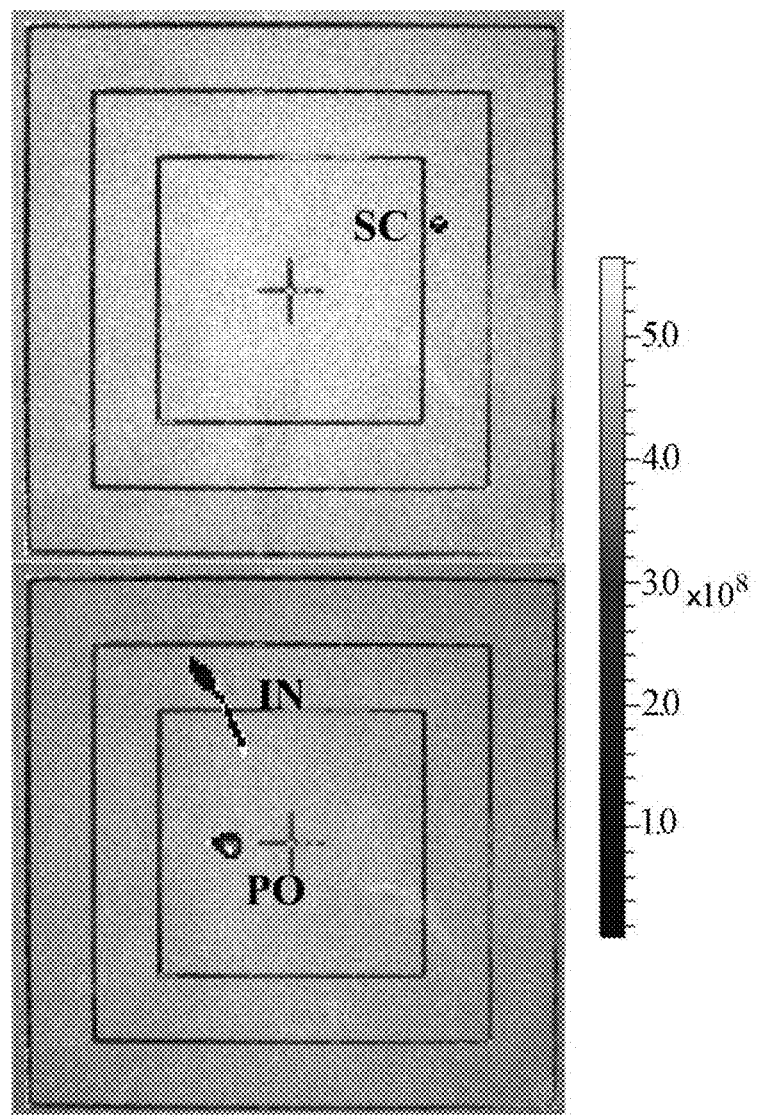
FIG. 43 shows the in vitro near-infrared fluorescence imaging of lymph node metastasis using the hybrid fluorescent conjugated polymer-based nanoprobe (in a NCI-H292 tumor model).

The results were specifically referred to FIGS. 42-43. As shown in the figures, after the hybrid $Gd^{3+}$ near-infrared fluorescent conjugated polymer-based nanoprobe was injected through the pad, the magnetic resonance signal and the near-infrared fluorescence signal of the nanoprobe were both detected in the popliteal lymph node PO, the sciatic lymph node SC and the inguinal lymph node IN.

Example 20

Magnetic Resonance Imaging and Near-Infrared Fluorescence Imaging of the Nanoprobe The mice were scanned in a $T_1$-weighted imaging mode using a 7.05 T MRI system (Biospec System 70/20, Brucker, Ettlingen, Germany) with a coil diameter of 40 mm. The mice with an axillary NCI-H292 tumor model were injected with a near-infrared fluorescent conjugated polymer-based nanoprobe simultaneously mixed with a gadolinium-containing magnetic resonance contrast agent DTPA-BSA (Gd) and a phospholipid folic acid through the tail vein, where the magnetic resonance signals were scanned respectively before and after the injection of the probe. The scanning parameters were set as follows: TE=6 ms; TR=1500 ms; Flip Angle=90 deg; Slice Thickness=1 mm; Field=7.05 T; and DFOV=25 mm. The MRI image exportation and the data analysis were performed using the ImageJ software. After the MRI experiment, the experimental mice were further scanned with a fluorescence imaging system to verify the signal distribution of the nanoprobe. The fluorescence imaging was performed using PerkinElmer's IVIS Lumina XRMS Series III imaging system, where the excitation wavelength was 460 nm and a 780 nm optical filter was provided in the receiving channel.

Figure 44:
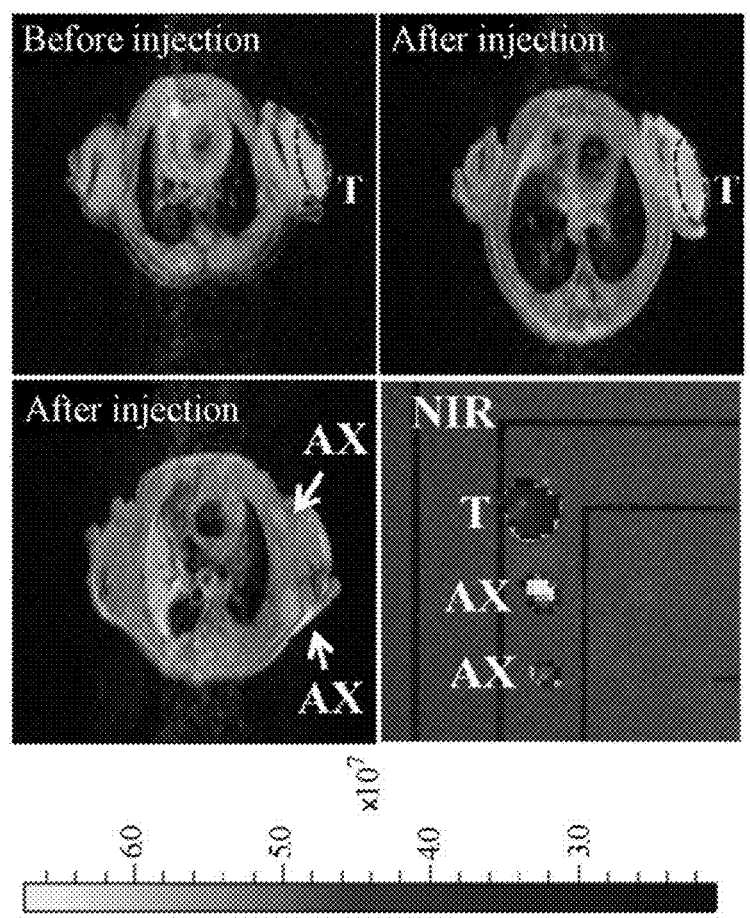
FIG. 44 shows the in vivo magnetic resonance imaging and the in vitro near-infrared fluorescence imaging of lymph node metastasis using the hybrid fluorescent conjugated polymer-based nanoprobe (in a NCI-H292 tumor model), where T indicates the tumor.

The results were specifically referred to FIG. 44. As shown in the figure, after the mice were injected with the hybrid $Gd^{3+}$ near-infrared fluorescent conjugated polymer-based nanoprobe through the tail vein, the magnetic resonance signal and the near-infrared fluorescence signal of the nanoprobe were detected in the tumor tissues and the two axillary lymph nodes AX.

Example 21

Fluorescence Imaging of the Nanoprobe

When the HeLa tumor grew to a diameter of 5-8 mm, the phospholipid folate-mixed PFBT near-infrared fluorescent conjugated polymer-based nanoprobe was simultaneously injected into the two pads of the mice to observe the targeting effect of the nanoprobe to the lymph node metastasis. The mice were in vivo imaged by PerkinElmer's IVIS Lumina XRMS Series III imaging system, where the excitation wavelength was 460 nm and a 780 nm optical filter was provided in the receiving channel.

Figure 45:
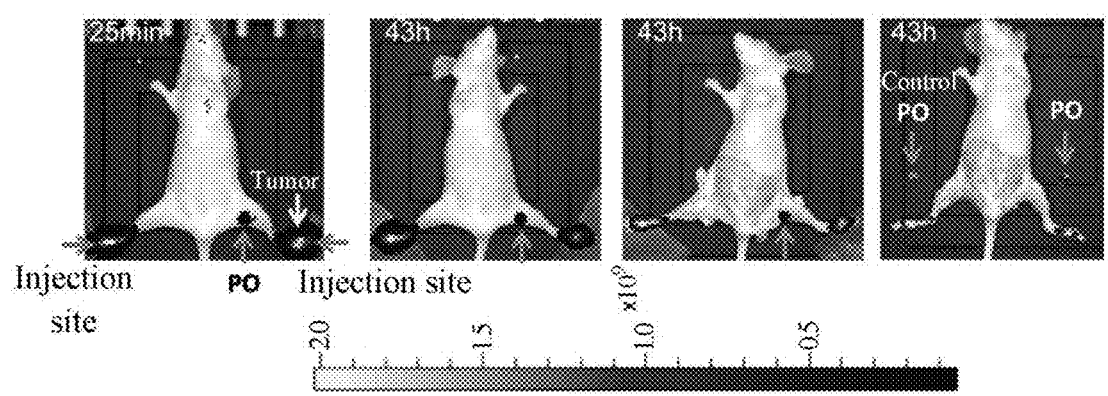
FIG. 45 shows the in vivo near-infrared fluorescence imaging of lymph node metastasis using the hybrid fluorescent conjugated polymer-based nanoprobe (in a HeLa tumor model).

The results were specifically referred to FIG. 45. As shown in the figure, after different times of the injection of the near-infrared fluorescent polymer-based nanoprobe through the pad, the near-infrared signal of the nanoprobe was detected in the popliteal lymph node PO at one side of the tumor but no probe signal was detected in the PO at the opposite side of the tumor. When the skin of the mouse was incised and two POs were taken out, it was confirmed that the near-infrared fluorescent signal of the probe was only detected in the PO at one side of the tumor. The results demonstrated that the nanoprobe can specifically and targetedly image the PO lymph node where tumor metastasis occurred.

Described above are merely preferred embodiments of the invention. It should be understood that those skilled in the art can make many modifications and variations based on the content disclosed by the invention. Therefore, the technical solution obtained by those skilled in the art through the combination of the prior art with logic analysis, ratiocination or limited experiments should fall within the scope defined by the appended claims.

What is claimed is:

1. A conjugated polymer-based nanoprobe, comprising:
    a fluorescent conjugated polymer;
    a surface ligand;
    a target molecule configured to recognize a folate receptor; and
    a near-infrared fluorescent dye, wherein the target molecule is a phospholipid-modified target molecule being one or more of a phosphatidylethanolamine-polyethylene glycol 5000-folic acid conjugate, a phosphatidylethanolamine-polyethylene glycol 2000-folic acid conjugate and a phosphatidylethanolamine-folic acid conjugate.

2. The conjugated polymer-based nanoprobe of claim 1, wherein the phospholipid modification is performed using a liposome.

3. The conjugated polymer-based nanoprobe of claim 1, wherein the surface ligand is a surface ligand modified with a terminal carboxyl and is selected from styrene-polyethylene glycol-carboxyl, polyethylene glycol-carboxyl, a styrene-maleic anhydride copolymer or a combination thereof.

4. The conjugated polymer-based nanoprobe of claim 1, wherein an absorption wavelength of the near-infrared fluorescent dye is 700-900 nm; and the near-infrared fluorescent dye is selected from the group consisting of NIR775, DiIC18, ICG, Cy7 and Cy7.5.

5. The conjugated polymer-based nanoprobe of claim 1, wherein the fluorescent conjugated polymer is selected from PFBT or MEH-PPV; and a molecular weight of PFBT is 10,000-52,000 and a molecular weight of MEH-PPV is 10,142-200,000.

6. The conjugated polymer-based nanoprobe of claim 1, wherein the near-infrared fluorescent dye is 0.2%-1.2% by weight of the fluorescent conjugated polymer; a weight ratio of the surface ligand to the fluorescent conjugated polymer is 0.5-2:1; and a weight ratio of the target molecule to the fluorescent conjugated polymer is 0.2-1:1.

7. The conjugated polymer-based nanoprobe of claim 1, wherein using a transmission electron microscope, the conjugated polymer-based nanoprobe has an average particle size of 2-100 nm, preferably 20-60 nm.

8. The conjugated polymer-based nanoprobe of claim 1, further comprising a gadolinium-containing magnetic resonance contrast agent.

9. The conjugated polymer-based nanoprobe of claim 8, wherein the gadolinium of the gadolinium-containing magnetic resonance contrast agent is phospholipid-modified gadolinium.

10. The conjugated polymer-based nanoprobe of claim 9, wherein the phospholipid-modified gadolinium is a phospholipid-modified gadolinium-diethylenetriaminepentaacetic acid complex; and the phospholipid-modified gadolinium-diethylenetriaminepentaacetic acid complex is selected from DTPA-BSA (Gd), bis(18:0 PE)-DTPA (Gd), bis(16:0 PE)-DTPA (Gd), bis(14:0 PE)-DTPA (Gd), 18:0 PE-DTPA (Gd), 16:0 PE-DTPA (Gd) or a combination thereof.

11. The conjugated polymer-based nanoprobe of claim 8, wherein the near-infrared fluorescent dye is 0.2%-1.2% by weight of the fluorescent conjugated polymer; a weight ratio of the surface ligand to the fluorescent conjugated polymer is 0.5-2:1; a weight ratio of the target molecule to the fluorescent conjugated polymer is 0.2-1:1; and a weight ratio of the gadolinium-containing magnetic resonance contrast agent to the fluorescent conjugated polymer is 3-5:1.

12. The conjugated polymer-based nanoprobe of claim 9, wherein using a transmission electron microscope, the conjugated polymer-based nanoprobe has an average particle size of 20-130 nm, preferably 30-60 nm.

13. A method for preparing the conjugated polymer-based nanoprobe of claim 8, comprising:
    (1) adding the fluorescent conjugated polymer, the surface ligand, the near-infrared fluorescent dye, the target molecule and the gadolinium-containing magnetic resonance contrast agent to an organic solvent followed by ultrasonication to obtain a mixture;

(2) adding the mixture to ultrapure water under ultrasonication and continuously ultrasonicating the reaction mixture; and (3) introducing nitrogen to the reaction mixture under heating at 45-55° C. to volatilize the organic solvent to produce the conjugated polymer-based nanoprobe.

14. The method of claim 13, wherein the gadolinium of the gadolinium-containing magnetic resonance contrast agent is phospholipid-modified gadolinium.

15. The method of claim 13, wherein in step (1),
the organic solvent is tetrahydrofuran or chloroform; the near-infrared fluorescent dye is 0.2%-1.2% by weight of the fluorescent conjugated polymer; a weight ratio of the surface ligand to the fluorescent conjugated polymer is 0.5-2:1; a weight ratio of the target molecule to the fluorescent conjugated polymer is 0.2-1:1; and a weight ratio of the gadolinium-containing magnetic resonance contrast agent to the fluorescent conjugated polymer is 3-5:1; and in step (2), a power for ultrasonication is set to 8-12%, the ultrasonication is performed for 4-6 s every other 2-4 s; and a total ultrasonication time is set to 50-70 s.

16. A method for targeted imaging of lymph node metastasis based on a conjugated polymer-based nanoprobe, comprising:

(1) preparing a molecular imaging agent comprising the conjugated polymer-based nanoprobe of claim 8; and (2) detecting the lymph node metastasis by near-infrared fluorescence imaging, photoacoustic imaging and/or magnetic resonance imaging using the molecular imaging agent.

17. The method of claim 16, wherein the conjugated polymer-based nanoprobe is capable of targetedly imaging tumor cells expressing a folate receptor at the cellular level.

18. The method of claim 16, wherein the conjugated polymer-based nanoprobe is capable of recognizing a normal lymph node and a lymph node with tumor metastasis.

* * * * *